United States Patent [19]
Boden et al.

[11] 4,374,277
[45] Feb. 15, 1983

[54] ALIPHATIC $C_{11}$ BRANCHED CHAIN ALDEHYDES AND ALCOHOLS, PROCESS FOR PREPARING SAME AND USES THEREOF IN AUGMENTING OR ENHANCING THE AROMA OF PERFUMES, COLOGNES AND/OR PERFUMED ARTICLES

[75] Inventors: Richard M. Boden, Monmouth Beach; John H. Geiger, Jr., Lakewood, both of N.J.

[73] Assignee: International Flavors & Fragrances Inc., New York, N.Y.

[21] Appl. No.: 305,533

[22] Filed: Sep. 25, 1981

Related U.S. Application Data

[62] Division of Ser. No. 233,861, Feb. 12, 1981, Pat. No. 4,304,689.

[51] Int. Cl.[3] ........................ C07C 47/02; C07C 45/50
[52] U.S. Cl. .................................... 568/448; 568/451; 568/909; 568/850
[58] Field of Search ................ 568/451, 448, 909, 850

[56] References Cited

U.S. PATENT DOCUMENTS

| | | | |
|---|---|---|---|
| 3,461,184 | 8/1969 | Hay | 260/683.15 |
| 3,538,181 | 11/1970 | Banks | 260/683.15 |
| 3,627,700 | 12/1971 | Zuech | 252/429 |
| 3,652,676 | 5/1972 | Kahle et al. | 568/909 |
| 3,984,478 | 10/1976 | Homier | 568/909 |
| 4,283,433 | 8/1981 | Pickenhagen | 568/448 |
| 4,304,689 | 12/1981 | Boden et al. | 252/522 |

OTHER PUBLICATIONS

Kurray, "Chemical Abstracts", vol. 93, (1980), p. 204,066f.

Murphy et al., "Ind. Eng. Chem., Prod. Res. Dev.", vol. 14, No. 3, (1975), p. 167.

Whitmore et al., "J. Amer. Chem. Soc.", vol. 68, Feb. 1946, p. 281.

Whitmore et al., "J. Amer. Chem. Soc.", vol. 67, Dec. 1945, p. 2158.

Wender et al., "Organic Synthesis Via Meta Carbonyls", vol. 2, pp. 43–63, 89, 91–95 and 137–139, Wiley–Interscience pub. 1977.

*Primary Examiner*—Werren B. Lone
*Attorney, Agent, or Firm*—Liberman, Arthur L.

[57] ABSTRACT

Described are branched chain $C_{11}$ aldehydes and alcohols, processes for producing same by (i) first dimerizing isoamylene(2-methyl-2-butene) to form a mixture of diisoamylenes and (ii) reacting the resulting mixture or separated components thereof with carbon monoxide and hydrogen by means of an oxo reaction, as well as methods for augmenting or enhancing the aroma of perfumes, colognes and perfumed articles by adding thereto perfume aroma augmenting or enhancing quantities of the thus produced $C_{11}$ branched chain aldehydes and alcohol compositions of matter. Also described are perfume compositions, colognes and perfumed articles including solid or liquid anionic, cationic, nonionic or zwitterionic detergents, fabric softener compositions, dryer-added fabric softener articles, hair preparations, deodorant compositions and bleaching compositions containing such products thus produced.

5 Claims, 17 Drawing Figures

GLC PROFILE FOR EXAMPLE I.

GLC PROFILE FOR EXAMPLE I.

GLC PROFILE FOR EXAMPLE I.

GLC PROFILE FOR EXAMPLE I.

GLC PROFILE FOR EXAMPLE I.

GLC PROFILE FOR EXAMPLE I.

GLC PROFILE FOR EXAMPLE I.
DISTILLATION PRODUCT.

GLC PROFILE FOR EXAMPLE I.
CRUDE PRODUCT.

FIG.2A
NMR SPECTRUM FOR PEAK I OF EXAMPLE I, OF GLC OF FIG. IE
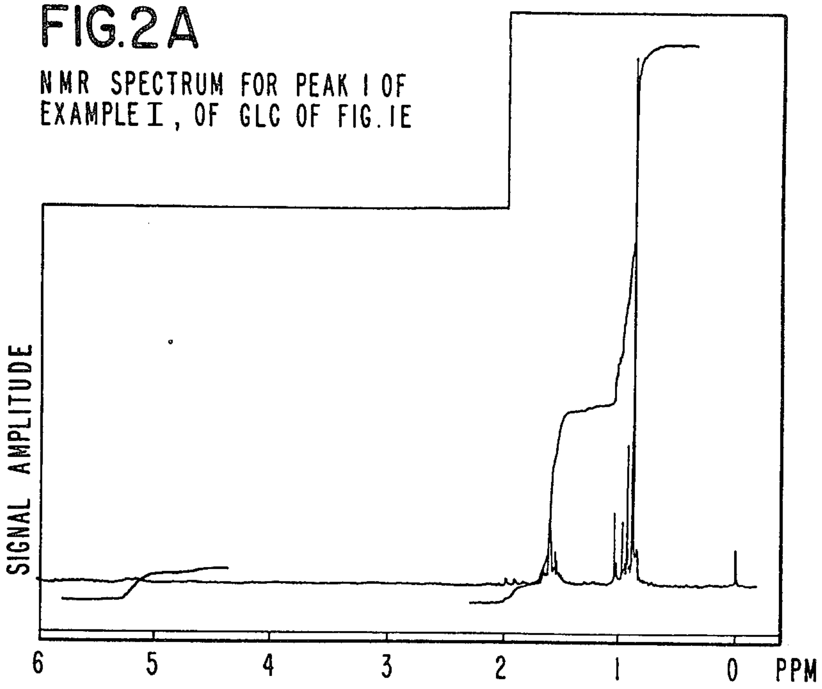
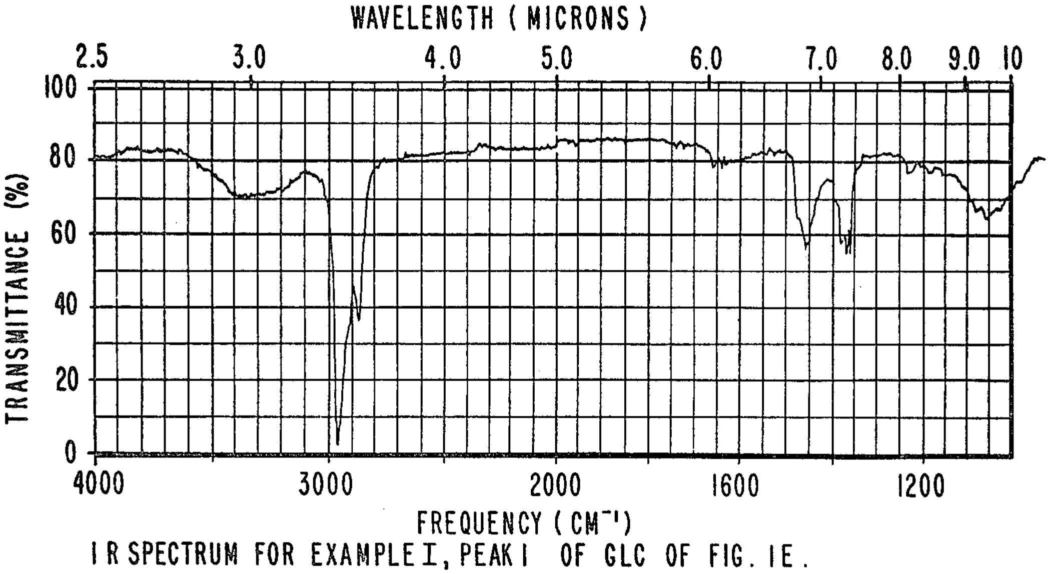
IR SPECTRUM FOR EXAMPLE I, PEAK I OF GLC OF FIG. IE.
FIG.2B FIG. 3A
NMR SPECTRUM FOR EXAMPLE I, PEAK 2, OF GLC OF FIG. 1E
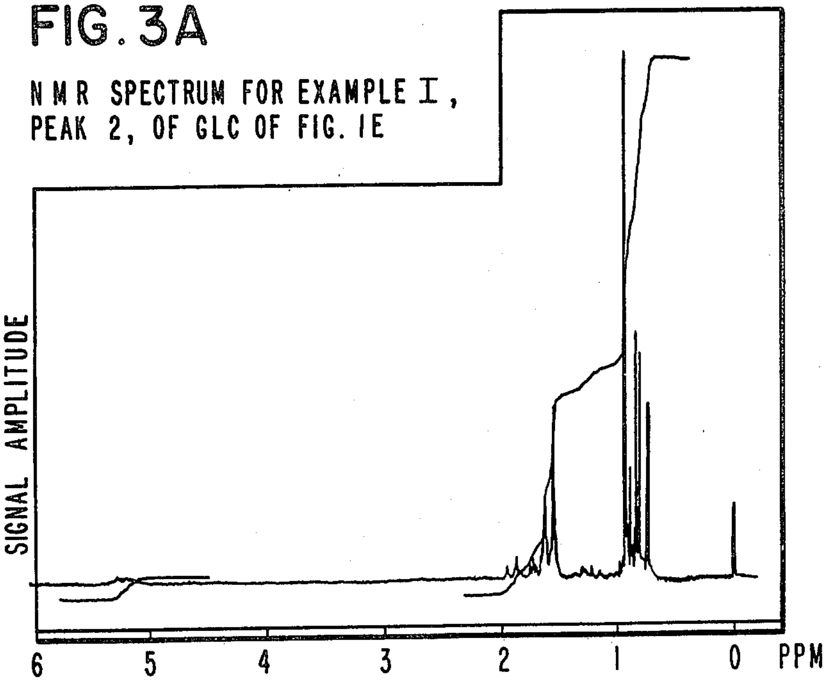
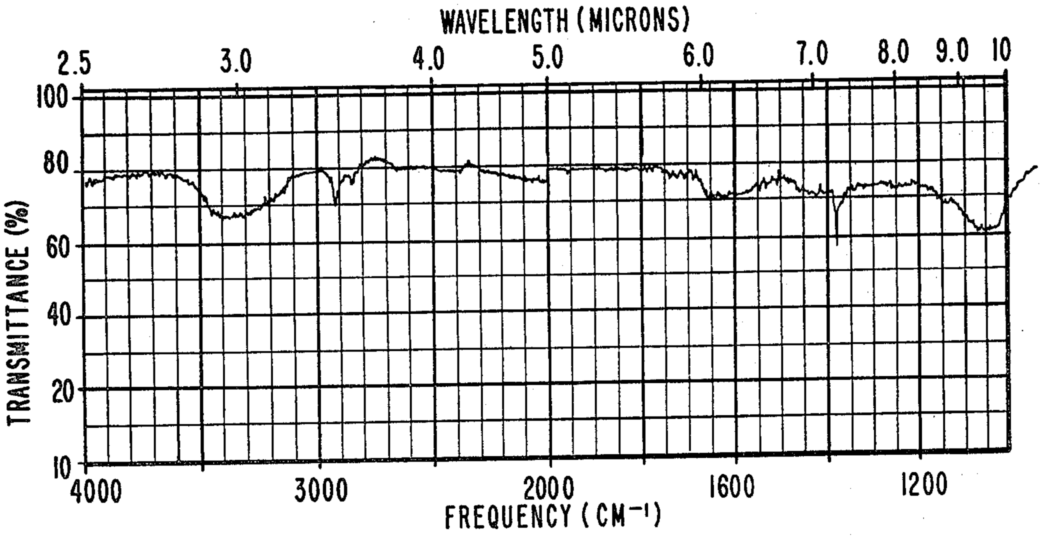
IR SPECTRUM FOR EXAMPLE I, PEAK 2 OF GLC OF FIG. 1E
FIG. 3B

NMR SPECTRUM FOR PEAK 2 OF EXAMPLE I, OF GLC OF FIG. 1B.

GLC PROFILE FOR EXAMPLE II.
CRUDE REACTION PRODUCT

GLC PROFILE FOR EXAMPLE II, DIISOUNDECANAL.

NMR SPECTRUM FOR EXAMPLE II, DIISOUNDECANAL.

I R SPECTRUM FOR EXAMPLE II, DIISOUNDECANAL.

GLC PROFILE FOR EXAMPLE II, DIISOUNDECANOL

IR SPECTRUM FOR EXAMPLE II, DIISOUNDECANOL.

ALIPHATIC $C_{11}$ BRANCHED CHAIN ALDEHYDES AND ALCOHOLS, PROCESS FOR PREPARING SAME AND USES THEREOF IN AUGMENTING OR ENHANCING THE AROMA OF PERFUMES, COLOGNES AND/OR PERFUMED ARTICLES

This application is a divisional of application for U.S. Pat. Ser. No. 233,861 filed on Feb. 12, 1981, now U.S. Pat. No. 4,304,689 issued on Dec. 8, 1981.

BACKGROUND OF THE INVENTION

The instant invention provides $C_{11}$ branched chain aldehydes and alcohols defined according to the generic structure:

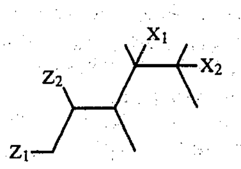

wherein one of $X_1$ or $X_2$ is hydrogen and the other of $X_1$ or $X_2$ is methyl; and wherein one of $Z_1$ or $Z_2$ is hydrogen and the other of $Z_1$ or $Z_2$ is hydroxymethyl having the structure:

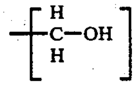

or carboxaldehyde having the structure:

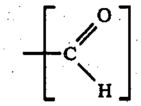

which are used to augment or enhance the aroma of perfume compositions, colognes or perfumed articles.

Inexpensive chemical compounds which can provide intense and long-lasting citrusy, green, melony, woody, peanut oil-like and vetiver-like aroma nuances are desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree, or they contribute undesirable or unwanted odor to the compositions.

$C_{11}$ aliphatic aldehydes and alcohols are well known in the art of perfumery, e.g., n-undecanal and n-undecanol. Oxo reaction products on hydrocarbon compounds are also well known in the perfumery industry. Thus, U.S. Pat. No. 4,146,505 discloses the formation of hydroxymethyl-formyl-tricyclo[5,2,1,$0^{2,6}$]decane having the structure:

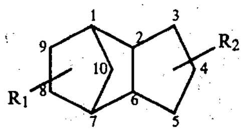

wherein $R_1$ and $R_2$ are the hydroxymethyl group, $CH_2OH$ or the formyl group CHO and $R_1$ represents $CH_2OH$ when $R_2$ is CHO and vice versa. This polycyclic carboxaldehyde alcohol is indicated to be useful as a musk aroma imparting or augmenting material. The material is indicated to be produced by reaction of carbon monoxide and hydrogen with dicyclopentadiene. Other oxo reaction products on unsaturated hydrocarbons are known in the perfumery industry, for example, "Vandor-B", which is the oxo reaction product of carbon monoxide and hydrogen on diiosbutylene. This material has been produced by International Flavors & Fragrances Inc., the assignee of the instant patent application, for several years.

Nothing in the prior art discloses the use of the $C_{11}$ aldehydes and alcohols produced by means of carrying out an "oxo" reaction (with carbon monoxide and hydrogen) on one or more diisoamylenes defined according to the generic structure:

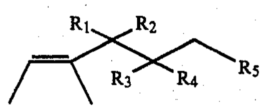

wherein $R_1$, $R_2$, $R_3$, $R_4$ and $R_5$ represent hydrogen or methyl with the proviso that (i) at least one of $R_1$ and $R_2$ represents methyl, (ii) at least one of $R_3$ and $R_4$ represents methyl, (iii) the sum of the carbon atoms in $R_1$, $R_2$, $R_3$, $R_4$ and $R_5$ is 3 and (iv) $R_1$ and $R_2$ represent hydrogen when $R_5$ is methyl; to produce one or more of the compounds defined according to the structure:

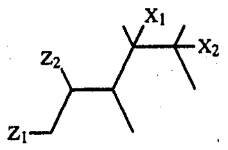

wherein one of $X_1$ or $X_2$ is hydrogen and the other of $X_1$ or $X_2$ is methyl; and wherein one of $Z_1$ or $Z_2$ is hydrogen and the other of $Z_1$ or $Z_2$ is hydroxymethyl having the structure:

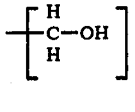

or carboxaldehyde having the structure:

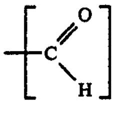

"Diisoamylene" is indicated to be synthesized in the following references:

(i) Murphy & Lane, Ind. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).

(ii) Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes).

(iii) Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

(iv) U.S. Pat. No. 3,627,700, issued on Dec. 14, 1971, (Zuech).

(v) U.S. Pat. No. 3,538,181, issued on Nov. 3, 1970 (Banks).

(vi) U.S. Pat. No. 3,461,184, issued on Aug. 12, 1969 (Hay, et al).

(vii) Tausz, Chemische Zentralblatt, 1919, II, 125 (Production of Di-isoamylene from Isoamylene Using Mercury Acetate Catalyst).

U.K. Pat. No. 796,130 published on June 4, 1958 discloses the synthesis of polyalkylindanes by means of, interalia, reacting alpha-methylstyrene with trimethylethene (2-methyl-butene-2) in the presence of an acid catalyst such as, sulfuric acid or boron trifluoride etherate. It is further indicated that such compounds are useful intermediates in the production of perfumery compounds. Apparently, however, the more volatile diisoamylenes produced as side-products in the reaction of 2-methyl-butene-2 with alpha-methylstyrene have heretofore been discarded.

Catalytic oxo reactions on 10-carbon atom containing olefins are known to have been carried out according to "Organic Syntheses Via Methyl Carbonyls" Volume 2 by Wender and Pino (Wiley-1977) at Table 5, page 63, wherein it is indicated that the olefin having the structure:

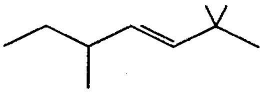

is reacted with carbon monoxide and hydrogen to produce a mixture of the three aldehydes having the structures:

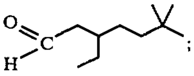
;
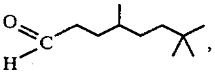
, and

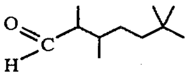

according to the reaction:

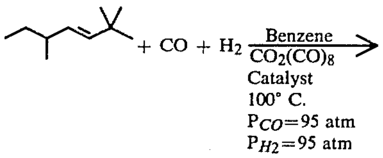

-continued

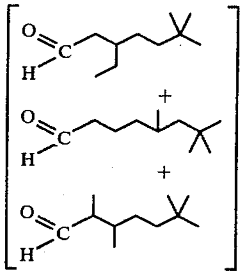

Chem. Abstracts, Volume 93, 1980, at 204066f discloses a summary of Japanese Kokia Tokkyo Koho 80-85,534 which discloses the reaction of diisobutylene with carbon monoxide in the presence of cobalt octacarbonyl, dioctylphosphine and dodecylbenzene at 120 kg/cm$^2$ and 150° C. for 5 hours yielding isononyl aldehyde and isononyl alcohol.

Nothing in the prior art, however, discloses the use of the oxo reaction product on diisoamylenes in augmenting or enhancing the aroma of perfume compositions, perfumed articles or colognes.

BRIEF DESCRIPTION OF THE DRAWINGS

FIG. 2A represents the NMR spectrum for Peak 1 of the GLC profile of FIG. 1E.

FIG. 2B represents the infra-red spectrum for Peak 1 of the GLC profile of FIG. 1E.

FIG. 3A represents the NMR spectrum for Peak 2 of the GLC profile of FIG. 1E.

FIG. 3B represents the infra-red spectrum for Peak 2 of the GLC profile of FIG. 1E.

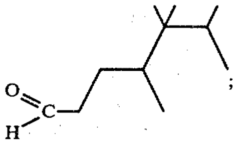
;
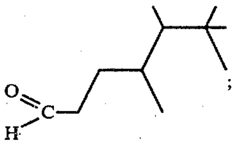
;

-continued

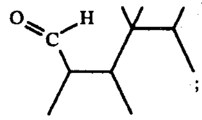
;
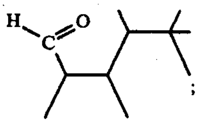
;

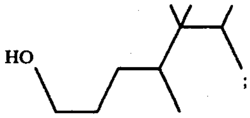
;
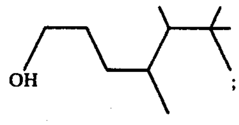
;

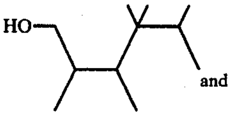
and
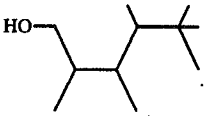
.

Figure 6:
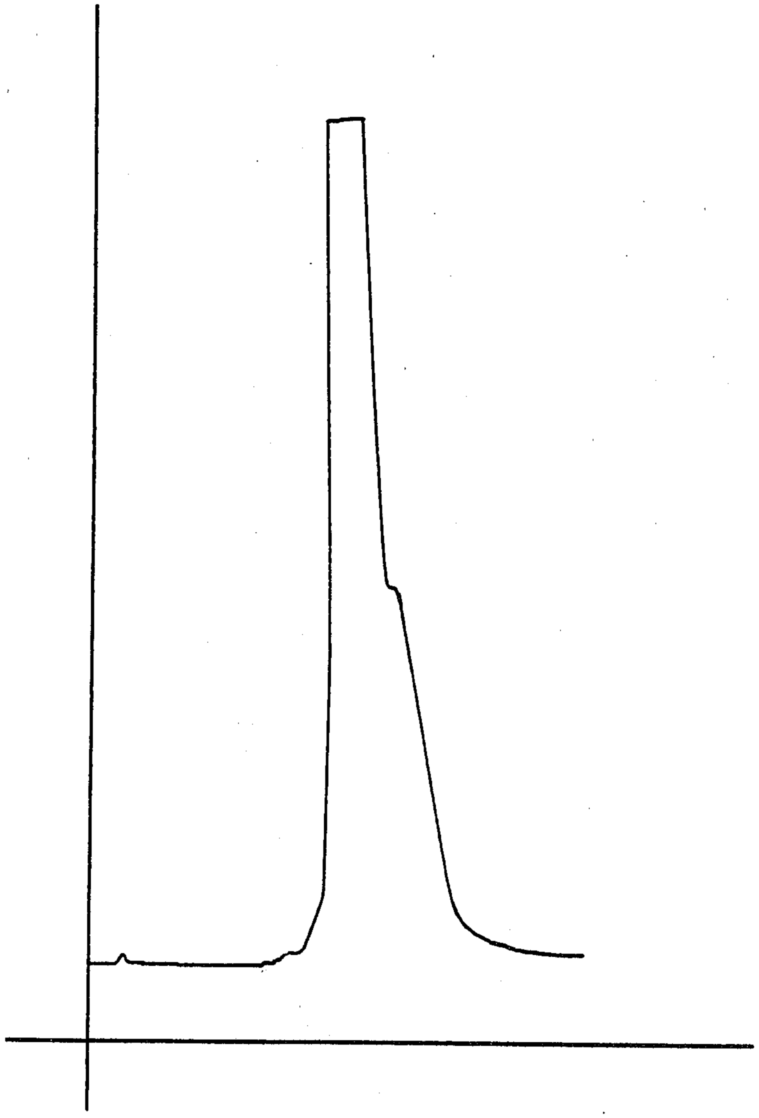

FIG. 6 is the GLC profile for the diisoundecanal compounds produced according to Example II having the structures:

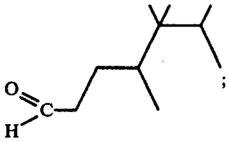
;
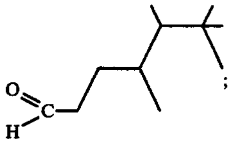
;

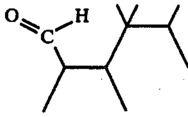
and
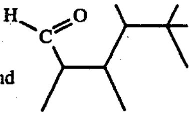

Figure 7:
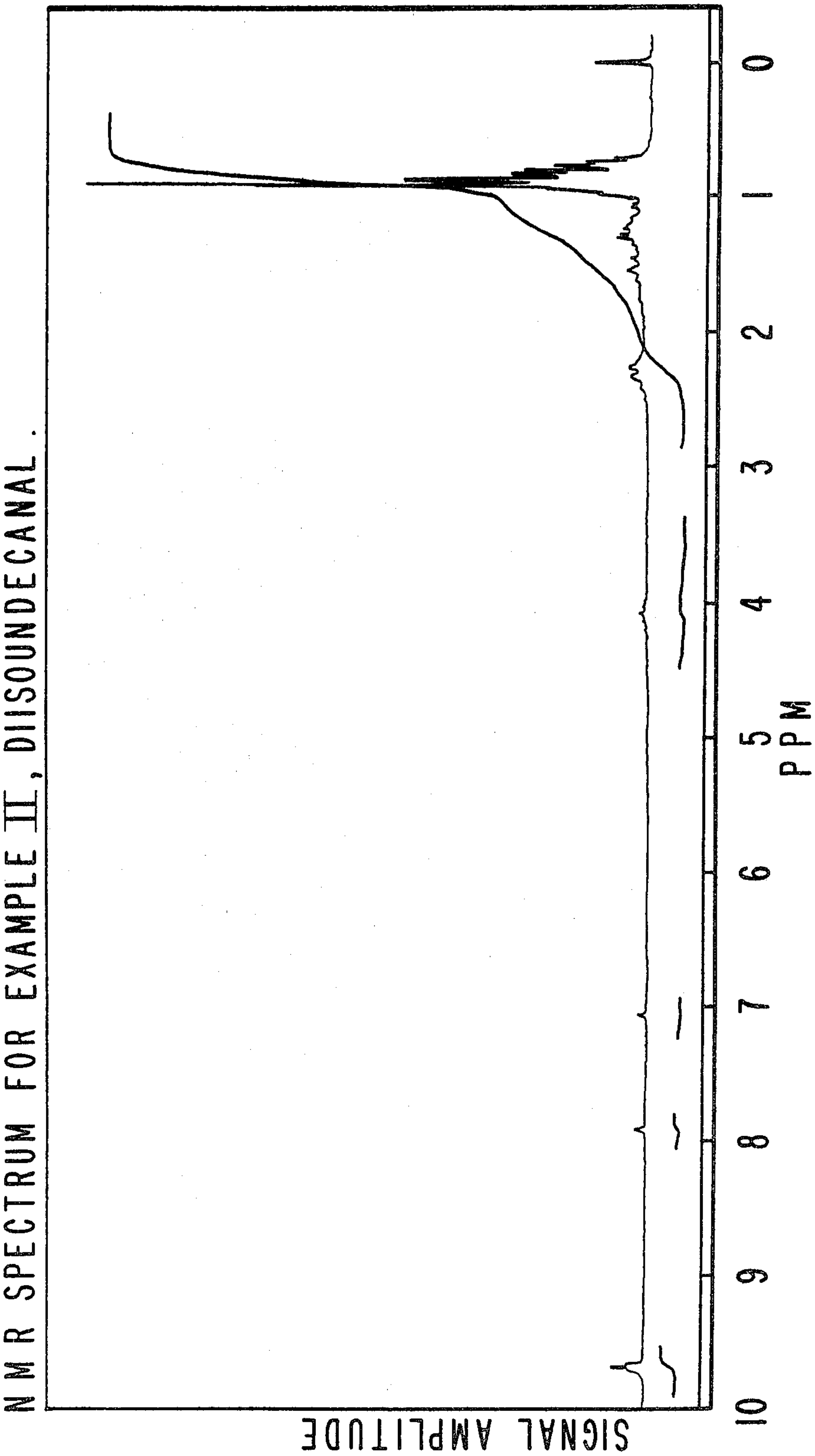

FIG. 7 is the NMR spectrum for the diisoundecanal compounds produced according to Example II having the structures:

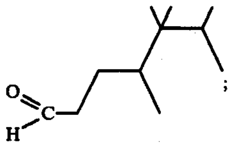
;
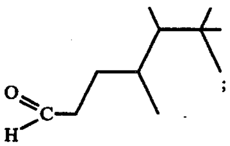
;

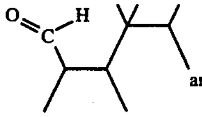
and
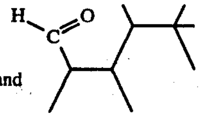

Figure 8:
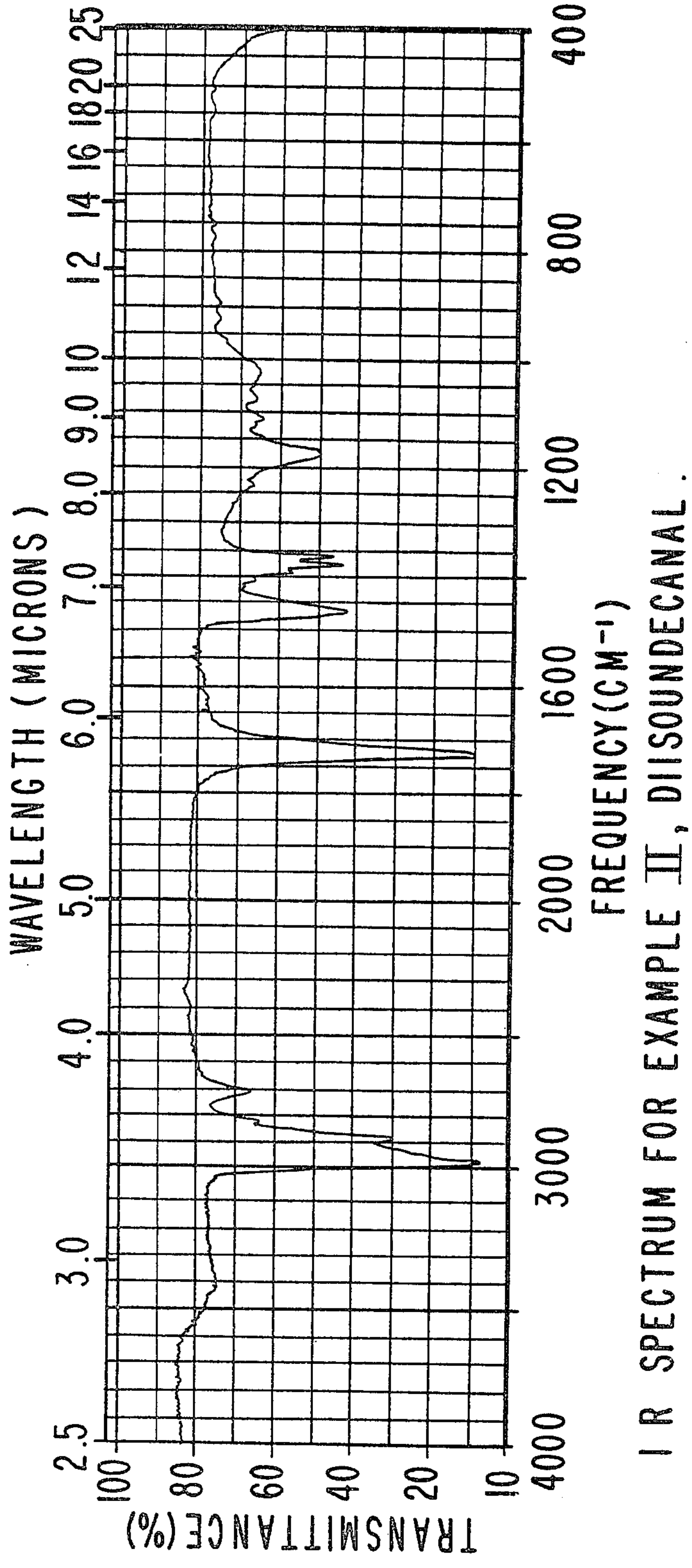

FIG. 8 is the infra-red spectrum for the diisoundecanal compounds produced according to Example II having the structures:

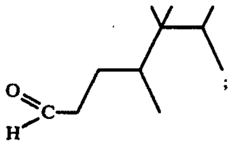
;
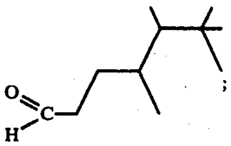
;

-continued

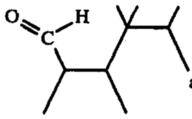
and
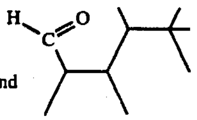

Figure 9:
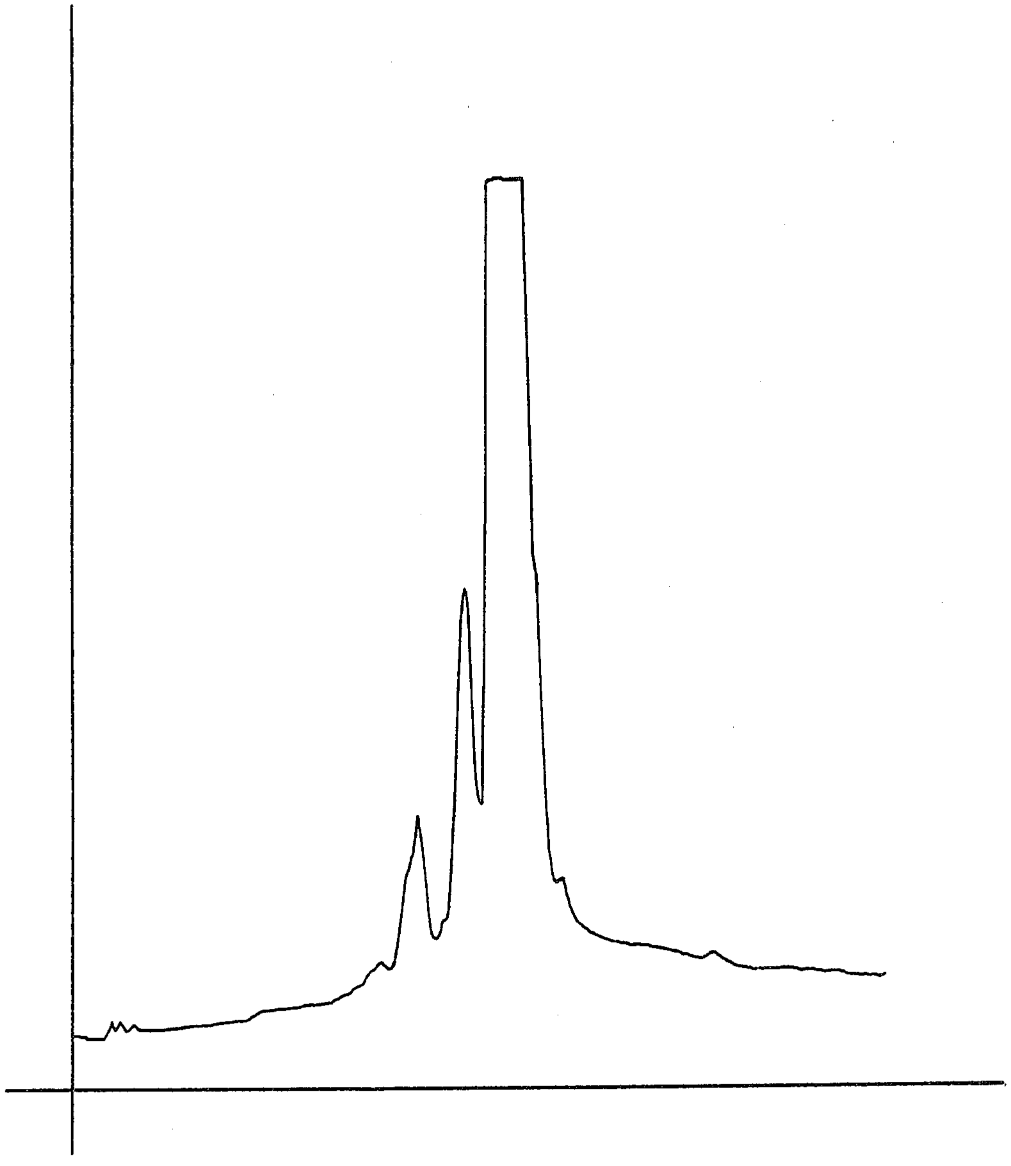

FIG. 9 is the GLC profile (conditions: SF-96, 6"×¼" 180° C. isothermal column) produced according to Example II containing the compounds having the structures:

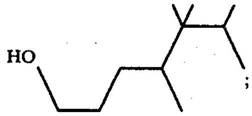
;
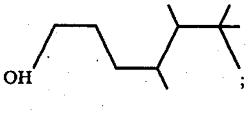
;

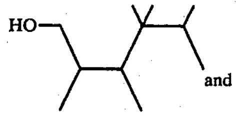
and
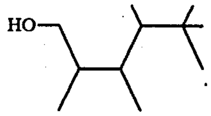
.

Figure 10:
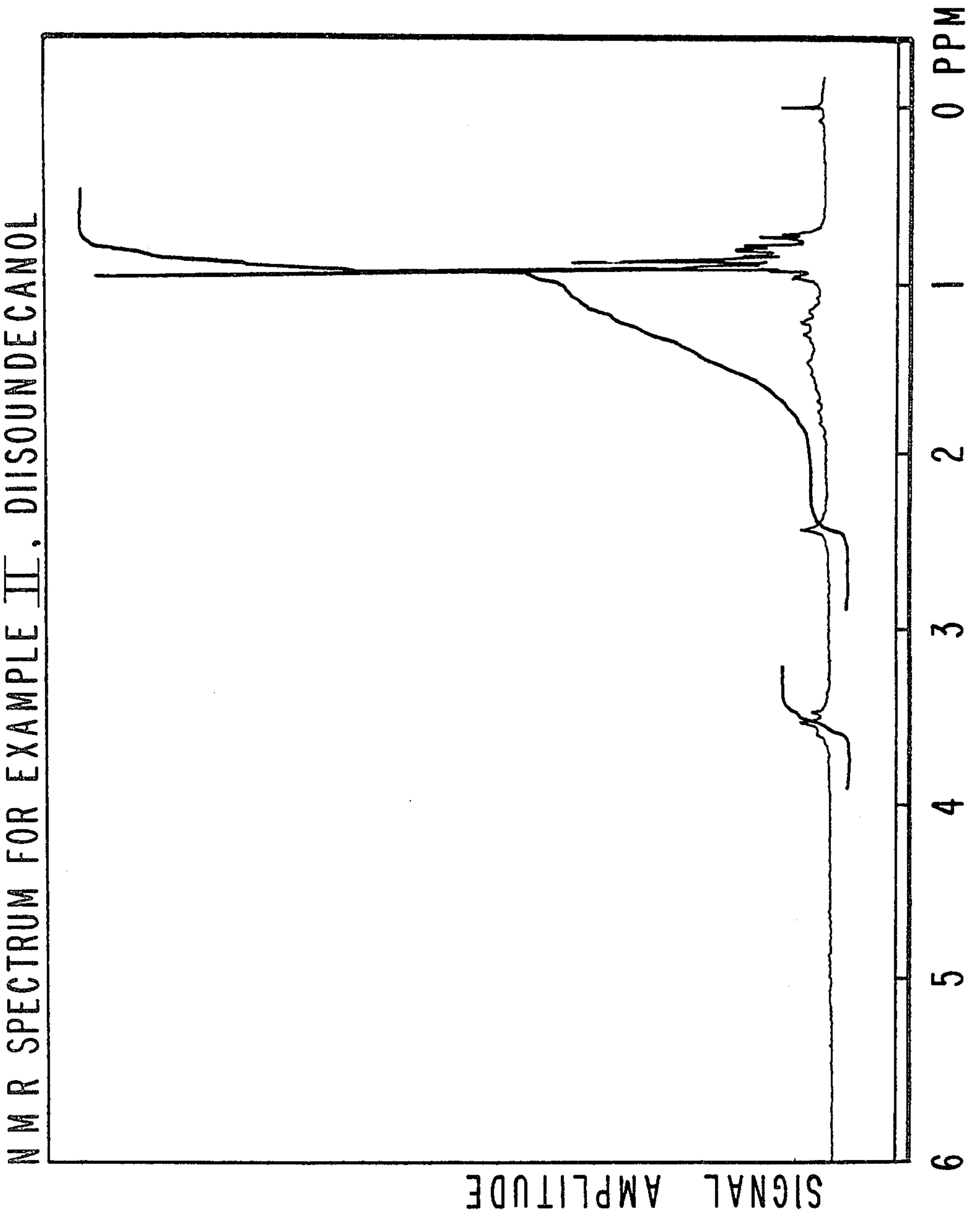

FIG. 10 is the NMR spectrum for the diisoundecanol compounds produced according to Example II having the structures:

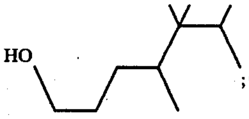
;
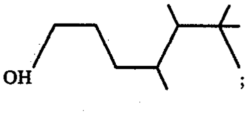
;

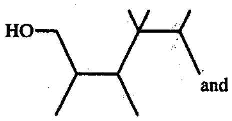
and
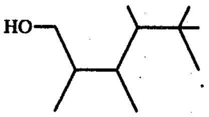
.

Figure 11:
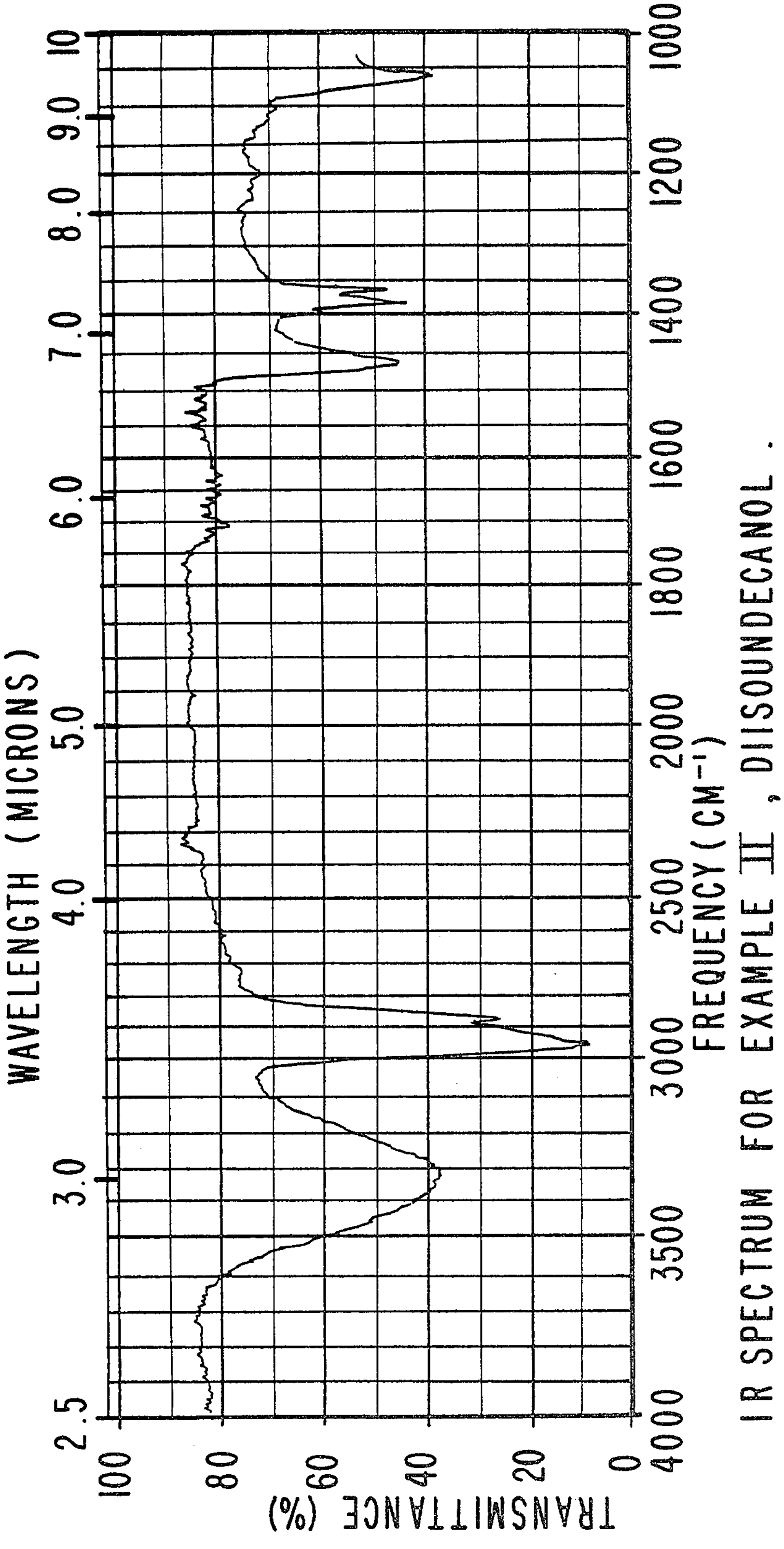

FIG. 11 is the infra-red spectrum for the diisoundecanol compounds produced according to Example II having the structures:

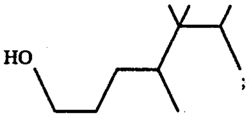
;
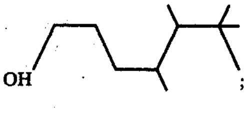
;

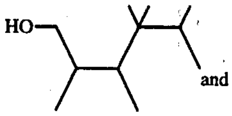
and
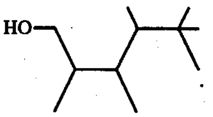
.

THE INVENTION

It has now been determined that $C_{11}$ branched chain aldehydes and alcohols defined according to the structure:

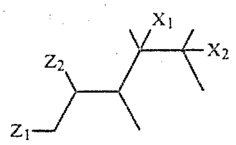

wherein one of $X_1$ or $X_2$ is hydrogen and the other of $X_1$ or $X_2$ is methyl and wherein one of $Z_1$ or $Z_2$ is hydroxymethyl having the structure:

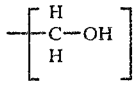

or carboxaldehyde having the structure:

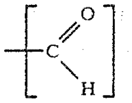

and the other of $Z_1$ or $Z_2$ is hydrogen produced according to the reactions:

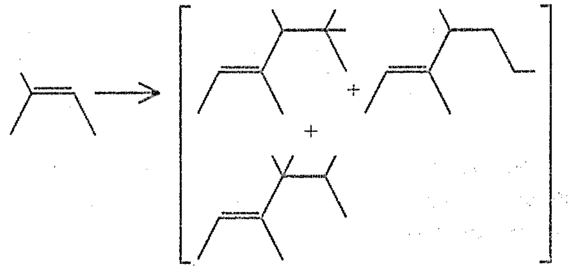

followed by, for example, the reaction:

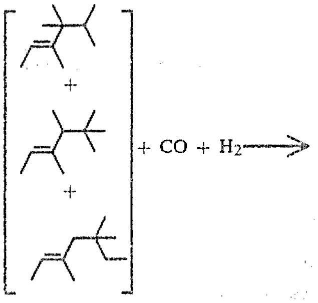

-continued

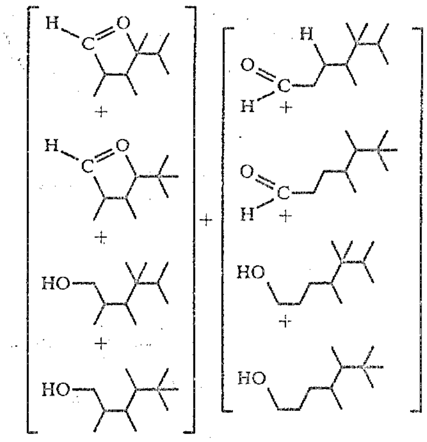

are capable of imparting or augmenting or enhancing a variety of fragrances in or to consumable materials.

Briefly, our invention contemplates augmenting or enhancing fragrances of such consumable materials as perfumes, perfumed articles, (e.g., solid or liquid anionic, cationic, nonionic or zwitterionic detergents, cosmetic powders, fabric softener compositions, dryer-added fabric softener articles and perfumed hypochlorite bleaches) and colognes by adding thereto a small, but effective, amount of at least one of the compounds defined according to the generic structure:

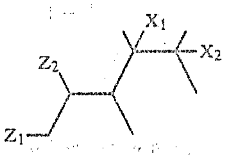

wherein one of $X_1$ or $X_2$ is hydrogen and the other of $X_1$ or $X_2$ is methyl and one of $Z_1$ or $Z_2$ is hydrogen and the other of $Z_1$ or $Z_2$ is hydroxymethyl having the structure:

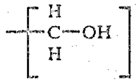

or carboxaldehyde having the structure:

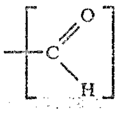

More specifically, the structures of the compounds useful in practicing our invention are as follows:

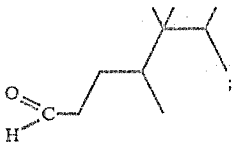
;

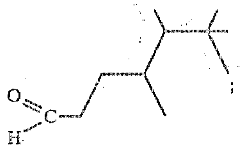
;

-continued

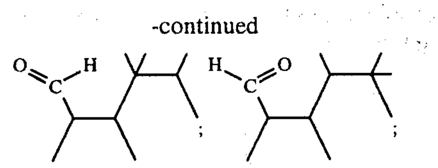

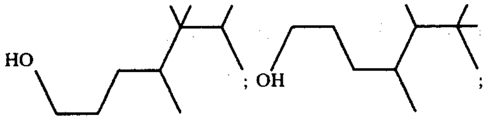

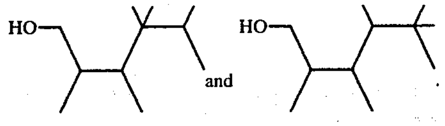
and

The $C_{11}$ branched chain aldehydes and alcohols of our invention augment or enhance green, citrusy, melony, woody, peanut oil-like and vetiver-like aroma characteristics. The perfumes, perfumed articles and colognes thereby causing one or more of said $C_{11}$ branched chain aldehyde and alcohol compounds to be useful particularly in citrus and vetiver-type fragrances.

The $C_{11}$ branched chain alcohol and aldehyde derivatives of our invention defined according to the structure:

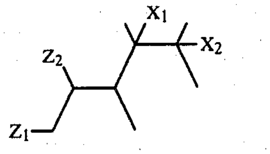

wherein one of $X_1$ or $X_2$ is hydrogen and the other of $X_1$ or $X_2$ is methyl and one of $Z_1$ or $Z_2$ is hydrogen and the other of $Z_1$ or $Z_2$ is hydroxymethyl having the structure:

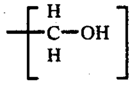

or carboxaldehyde having the structure:

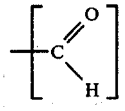

may be prepared by first (i) reacting 2-methyl-2-butene in the presence of an acidic catalyst which may be a Lewis acid such as, zinc chloride, aluminum chloride, aluminum bromide, diethyl aluminum chloride, diethyl aluminum bromide, ethyl aluminum dichloride, and diethyl aluminum bromide, boron trifluoride, boron trifluoride etherate, or any of the other catalysts enumerated in the following references:

(i) Murphy & Lane, Ind. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).

(ii) Whitmore & Mosher, Vol. 68, J. Am. Chem. Soc., February, 1946, p. 281 (Title: The Depolymerization of 3,4,5,5,-Tetramethyl-2-hexene and 3,5,5-Trimethyl-2-heptene in Relation to the Dimerization of Isoamylenes).

(iii) Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

(iv) U.S. Pat. No. 3,627,700, issued on Dec. 14, 1971, (Zuech).

(v) U.S. Pat. No. 3,638,181, issued on Nov. 3, 1970, (Banks).

(vi) U.S. Pat. No. 3,461,184, issued on Aug. 12, 1969, (Hay et al).

(vii) Gurwitsch, Chemische Berichte, 1912, Vol. 2, p. 796 (Production of Di-isoamylene From Isoamylene Using Mercury Acetate Catalyst).

and then (ii) reacting the resulting mixture or components thereof with a mixture of carbon monoxide and hydrogen using a particular range of temperatures and partial pressures of hydrogen and carbon monoxide over one of several alternative "oxo" type reaction catalysts over a period of residence times.

As to the reaction for forming the diisoamylene (i):

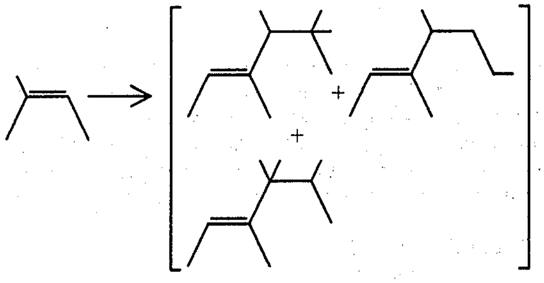

depending upon the conditions of reaction, including temperature, pressure, mole ratio of 2-methyl-2-butene:catalyst, concentration of 2-methyl-2-butene and solvent, concentration of catalyst and solvent and time of reaction, the ratio and natures of isomers of diisoamylene produced will vary in an as yet undetermined fashion. In any event, this invention contemplates the use of all isomers of diisoamylene as reactants defined according to the structures:

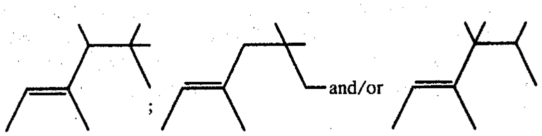
and/or taken alone or in admixture in all proportions, when used for the purpose of reaction with carbon monoxide and hydrogen.

As to the "oxo" reaction (ii) of the resulting diisoamylene derivatives with carbon monoxide and hydrogen carried out, for example, according to the reaction sequence:

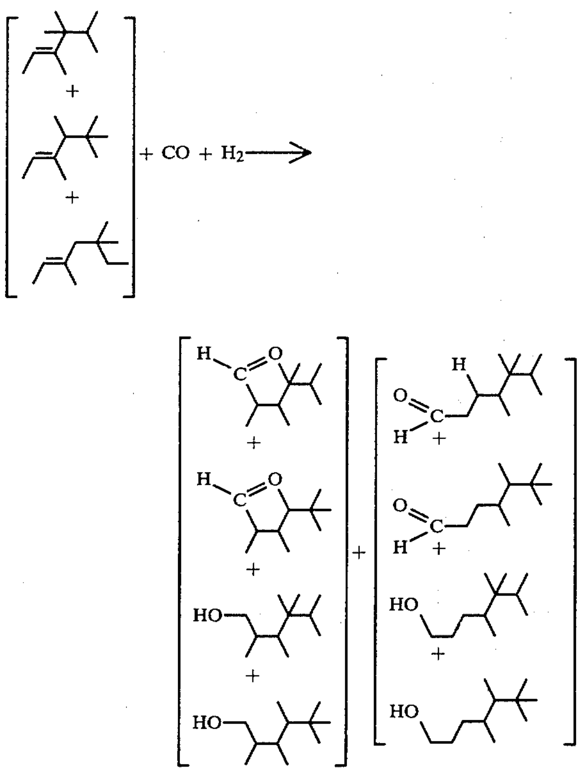

the reaction is carried out at temperatures of between 150° C. and 300° C. at pressures of between 50 and 250 atmospheres; with the ratio of partial pressure of carbon monoxide:hydrogen being from 0.1:1 up to 1:0.1. Any oxo type reaction catalyst but, most preferably, the catalyst to yield the best perfume mixtures are as follows:

Dicobalt octacarbonyl
Cobalt octanoate
Palladium chloride
Rhodium trichloride
Iron pentacarbonyl
Nickel tetracarbonyl
Polymer-bonded rhodium catalyst (e.g., rhodium bonded on a polystyrene substrate)
Tris-triphenyl phosphine rhodium-1-chloride Depending upon the conditions of reaction including, temperature, partial pressures of diisoamylene, carbon monoxide and hydrogen, mole ratio of diisoamylene:-catalyst, concentration of diisoamylene in solvent, concentration of catalyst in solvent and time of reaction, the ratio and nature of the isomers of aldehydes, the isomers of the alcohols and the ratio of the aldehydes to the alcohols will vary in an as yet undetermined fashion.

In any event, this invention contemplates all isomers of $C_{11}$ aldehydes and alcohols defined according to the structure:

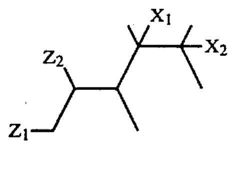

wherein one of $X_1$ or $X_2$ is hydrogen and the other of $X_1$ or $X_2$ is methyl; and wherein one of $Z_1$ or $Z_2$ is hydrogen and the other of $Z_1$ or $Z_2$ is hydroxymethyl having the structure:

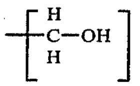

or carboxaldehyde having the structure:

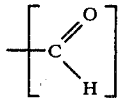

As olfactory agents, the $C_{11}$ branched chain alcohols and aldehydes taken alone or in admixture, of our invention, can be formulated into, or used as components of a "perfume composition" or can be used as components of a "perfumed article", or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils and hydrocarbons other than the $C_{11}$ branched chain alcohol and aldehyde derivatives of this invention which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation; and (d) top notes which are usually low boiling, fresh-smelling materials.

In perfume compositions, the individual component will contribute its particular olfactory characteristics, but the overall effect of the perfume composition will be the sum of the effects of each of the ingredients and in certian instances, a synergistic effect as a result of the addition of certain ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the $C_{11}$ branched chain alcohol and aldehyde derivatives of this invention which will be effective in perfume compositions depends on many factors, including the other ingredients, their amounts and the effects which are desired. It has been found that perfume compositions containing as little as 0.05% of the $C_{11}$ branched chain alcohol and aldehyde derivatives of this invention, or even less, can be used to impart an interesting, herbaceous, piney and woody aroma to soaps, liquid or solid anionic, cationic, nonionic or zwitterionic detergents, cosmetics, cosmetic powders, liquid and solid fabric softeners, dryer-added fabric softener articles, (e.g., BOUNCE® a registered trademark of the Procter & Gamble Company of Cincinnati, Ohio), optical brightener compositions and other products. The amount employed can range up to 70% or even higher, and will depend on considerations of cost, nature of the end product, and the effect desired on the finished product and particular fragrance sought. Thus, for example, when fragrancing liquid bleach compositions containing alkalihypochlorite such as, for example, sodium hypochlorite, for example CLOROX®, (registered trademark of Clorox, Inc.). The amount employed can be as high as 100% of the fragrance involved in the liquid bleach. Indeed, a distinctive aspect of our invention is the use of one or more of the $C_{11}$ branched chain alcohol and aldehyde derivatives of this invention in a stable liquid bleach composition.

The $C_{11}$ branched chain alcohol and aldehyde derivatives of this invention, taken alone or in admixture, can be used alone, or in a perfume composition as an olfactory component in detergents, soaps, space odorants and deodorants; perfumes; colognes, toilet waters; bath salts; hair preparations, such as lacquers, brilliantines, pomades and shampoos; cosmetic preparations, such as creams, deodorants, hand lotions, sunscreens; powders, such as talcs, dusting powders, face powders and the like; liquid bleaches, such as sodium hypochlorite-containing bleaches; floor waxes; automobile aromas and automobile polish compositions. When used as an olfactory component of a perfumed article, as little as 0.01% of one or more of the $C_{11}$ branched chain alcohol and aldehyde derivatives of this invention will suffice to impart an interesting, herbaceous, piney and woody aroma. Generally, no more than 0.5% is required to impart such aromas, however, in view of the rather low cost of the $C_{11}$ branched chain alcohol and aldehyde derivatives of this invention, up to 100% of the perfume composition can be one or more of the $C_{11}$ branched chain alcohol and aldehyde derivatives of this invention.

In addition, the perfume composition can contain a vehicle or carrier for the $C_{11}$ branched chain alcohol and aldehyde derivatives of this invention, alone, or with other ingredients. The vehicle can be a liquid such as a non-toxic alcohol such as ethanol, a glycol such as proplyene glycol, or the like. The carrier can be an absorbent solid, such as a gum or components for encapsulating the composition such as gelatin which can be used to form a capsule wall surrounding the perfume oil, as by means of coacervation.

It will thus be apparent that the $C_{11}$ branched chain alcohol and aldehyde derivatives of this invention can be utilized to alter, modify, augment or enhance sensory properties, particularly organoleptic properties such as fragrances of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF DIISOAMYLENE DERIVATIVES

Reaction:

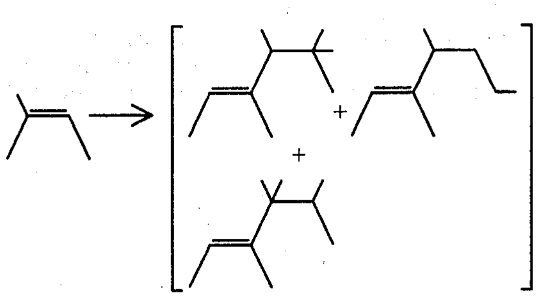

Diisoamylene is prepared according to one of the procedures set forth in the following references:

(i) Murphy & Lane, Ind. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).

(ii) Whitmore & Mosher, Vol. 68, J. Am. Chem. Soc., February, 1946, p. 281 (Title: The Depolymerization of 3,4,5,5-Tetramethyl-2-hexene and 3,5,5,-Trimethyl-2-heptene in Relation to the Dimerization of Isoamylenes).

(iii) Whitmore & Stahly, Vol. 67, J. Am. Chem. Soc., December, 1945, p. 2158 (Title: The Polymerization of Olefins. VIII The Polymerization of Olefins in Relation to Intramolecular Rearrangements. II).

(iv) U.S. Pat. No. 3,627,700 issued on Dec. 14, 1971, (Zuech).

(v) U.S. Pat. No. 3,538,181 issued on Nov. 3, 1970, (Banks).

(vi) U.S. Pat. No. 3,461,184 issued on Aug. 12, 1969 (Hay, et al).

(vii) Gurwitsch, Chemische Berichte, 1912, Vol. 2, p. 796 (Production of Di-isoamylene From Isoamylene Using Mercury Acetate Catalyst).

As an illustration, and not by way of limitation, the following example sets forth the preparation of diisoamylenes useful in producing the fragrances of our invention.

Over a period of ten hours, 2-methyl-2-butene is pumped through a $5' \times \frac{5}{8}$ (0.625 inch) tube packed with 15.0 grams of polystyrene sulfonic acid catalyst, at a temperature of 100° C. and at a pressure of 400 psig.

The resulting material was distilled in a fractionation column in order to separate the diisoamylene from the higher molecular weight polymers, which are formed during the reaction as by-products.

Figure 1A:
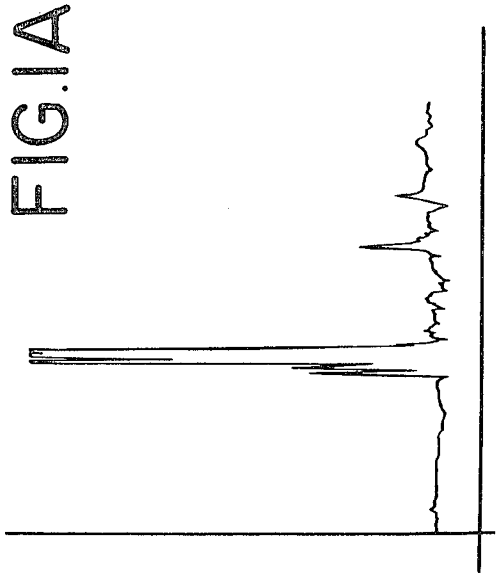
FIG. 1A represents the GLC profile for the reaction product of Example I using a 70% sulfuric acid catalyst at 35° C.

FIG. 1A represents the GLC profile for the reaction product of Example I using a 70% sulfuric acid catalyst at 35° C.

Figure 1B:
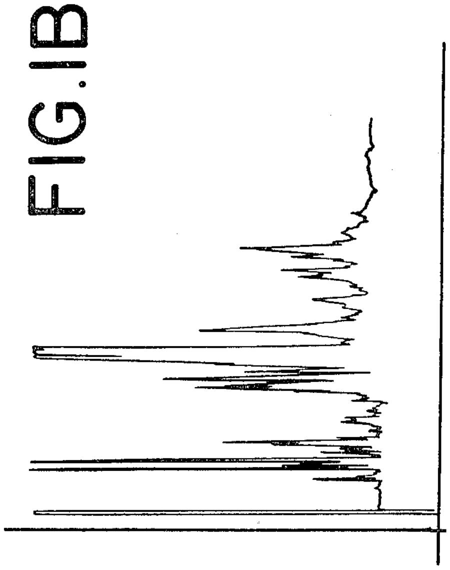
FIG. 1B represents the GLC profile for the reaction product of Example I using an Amberlyst® 15 acidic ion exchange resin catalyst at a temperature of 150° C.

FIG. 1B represents the GLC profile for the reaction product of Example I using an Amberlyst® 15 acetic ion exchange resin catalyst at a temperature of 150° C.

Figure 1C:
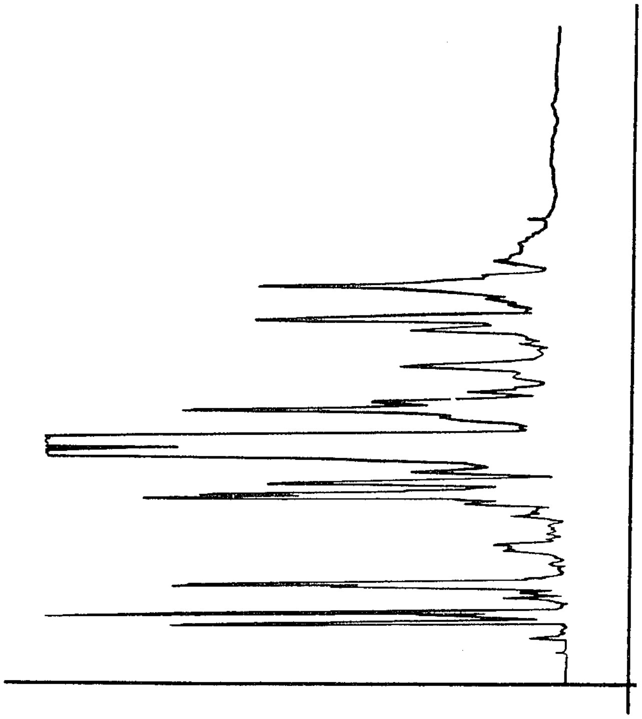
FIG. 1C represents the GLC profile for the reaction product of Example I, using an Amberlyst® 15 catalyst at 100° C.

FIG. 1C represents the GLC profile for the reaction product of Example I, using an Amberlyst® 15 catalyst at 100° C.

Figure 1E:
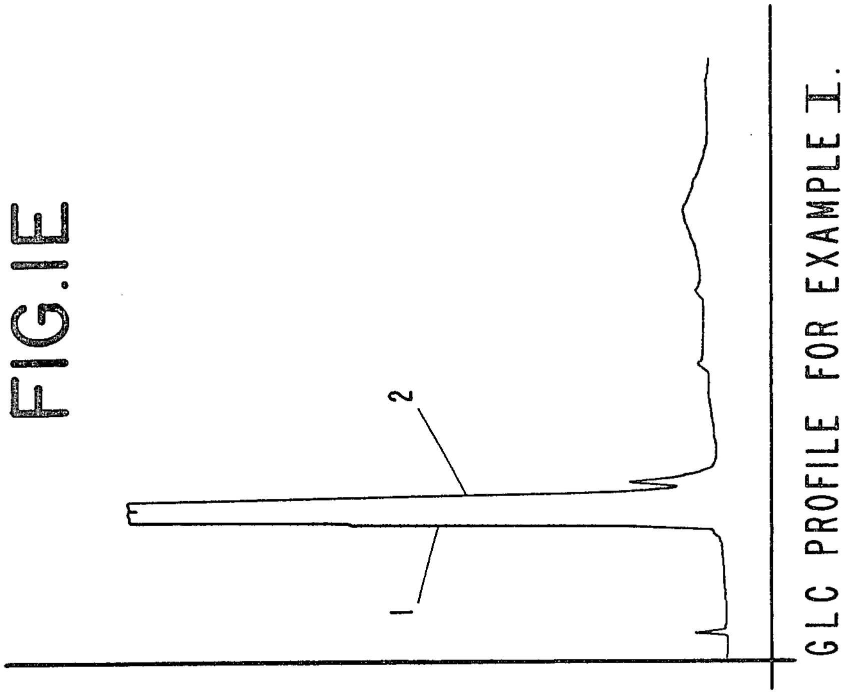
FIG. 1E represents the GLC profile for the reaction product of Example I, using a sulfuric acid catalyst, at 35° C. and an alpha-methylstyrene diluent according to the conditions of U.K. Patent Specification 796,130 (distilled reaction product).
Figure 1D:
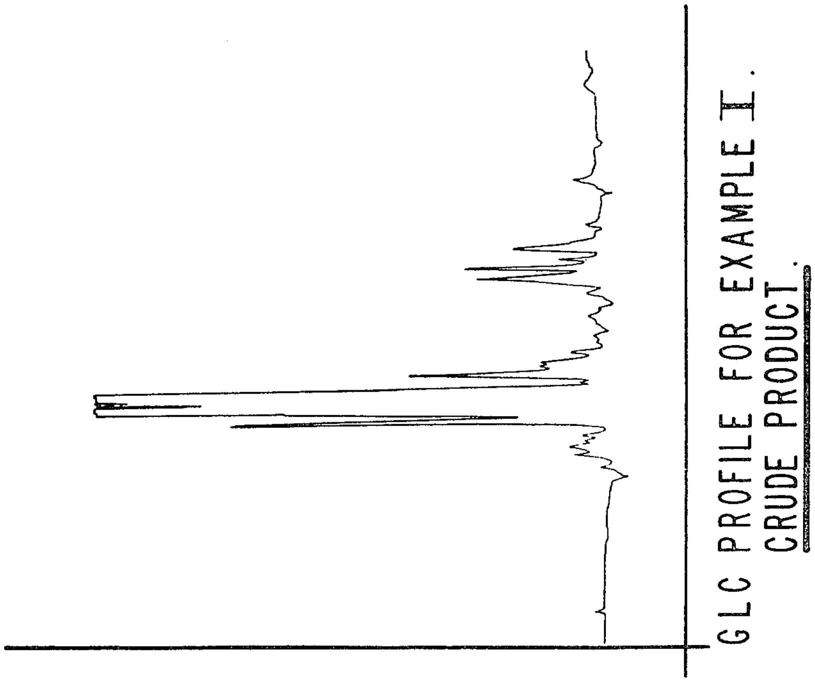
FIG. 1D represents the GLC profile for the reaction product of Example I, using a sulfuric acid catalyst and an alpha-methylstyrene diluent at 35° C. according to the conditions of U.K. Patent Specification 796,130 (crude reaction product).

FIG. 1D represents the GLC profile for the reaction product of Example I, using a sulfuric acid catalyst and an alpha-methylstyrene diluent at 35° C. according to the conditions of U.K. Patent Specification No. 796,130 (crude reaction product).

FIG. 1E represents the GLC profile for the reaction product of Example I, using a sulfuric acid catalyst, at 35° C. and an alpha-methylstyrene diluent according to the conditions of U.K. Patent Specification No. 796,130 (distilled reaction product).

FIG. 2A represents the NMR spectrum for Peak 1 of the GLC profile of FIG. 1E. Peak 1 has been determined by analysis to be the compound having the structure:

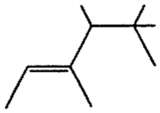

FIG. 2B represents the infra-red spectrum for Peak 1 of the GLC profile of FIG. 1E.

FIG. 3A represents the NMR spectrum for Peak 2 of the GLC profile of FIG. 1E. Peak 2 contains compounds having the structures:

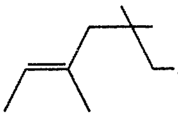
and
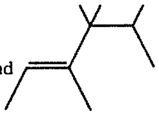

FIG. 3B represents the infra-red spectrum for Peak 2 of the GLC profile of FIG. 1E.

Figure 4:
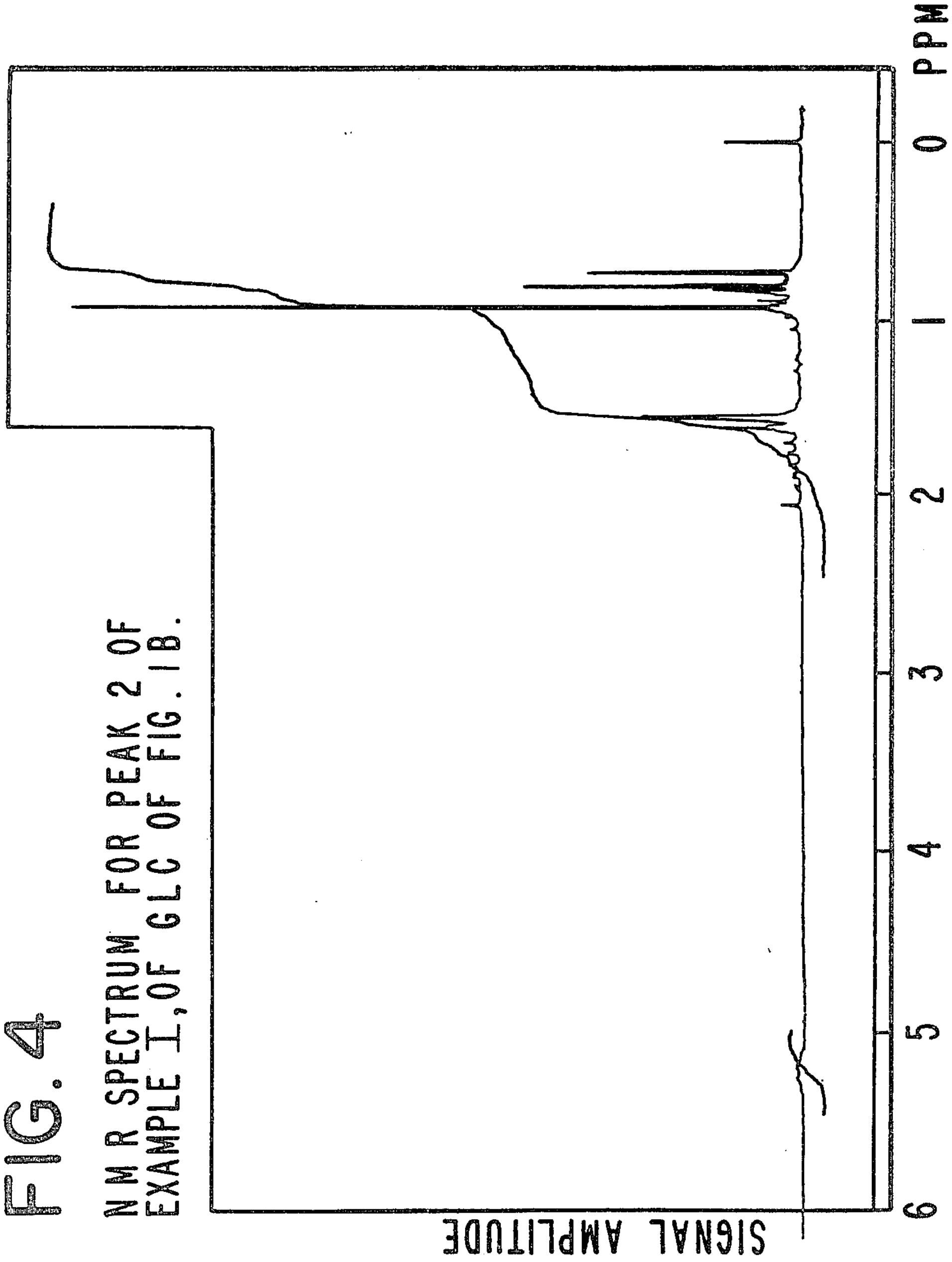
FIG. 4 represents the NMR spectrum for Peak 2 of the GLC profile of FIG. 1B.

FIG. 4 represents the NMR spectrum for Peak 2 of the GLC profile of FIG. 1B.

EXAMPLE II

PREPARATION OF MIXTURE OF DIISOUNDECANALS AND DIISOUNDECANOLS VIA OXO REACTIONS

Reaction:

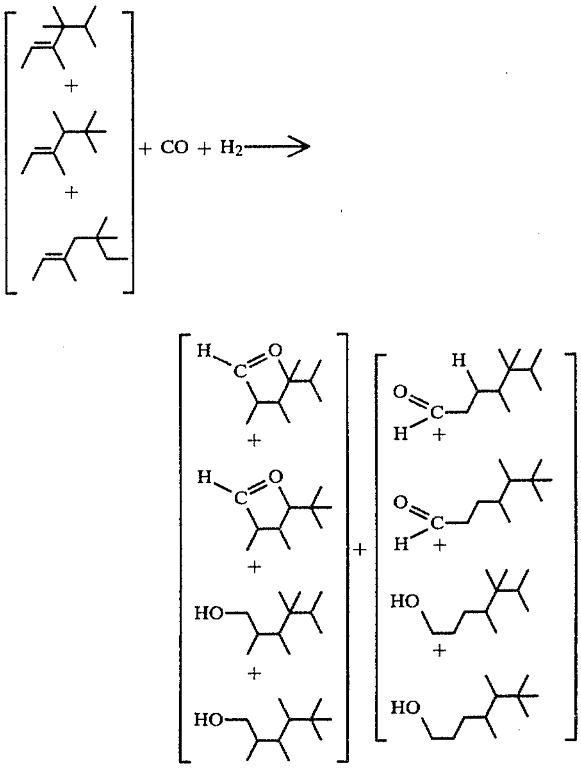

2500 ml (1835.5 grams) of the diisoamylene prepared according to Example I is intimately admixed with 200 ml (182 grams) of cobalt octoate in 200 cc of toluene. The reaction mass is placed in a 3 liter autoclave and pressurized to 2500 psig while heating the contents of the autoclave to a temperature in the range of 180°-204° C. The partial pressure of the hydrogen gas is 1000 pounds per square inch and the partial pressure of the carbon monoxide is 1500 pounds per square inch gauge. The contents of the autoclave are maintained at 180°-204° C. for 4 hours whereupon the autoclave is depressurized and the contents are filtered. The toluene solvent is evaporated and the reaction product is then distilled on a 2" splash column yielding the following fractions:

| Fraction Number | Vapor Temp. (°C.) | Liquid Temp. (°C.) | Head Vac. mm Hg. | Weight of Fraction |
|---|---|---|---|---|
| 1 | 28/81 | 52/52 | 40/50 | 190 |
| 2 | 64 | 78 | 25 | 190 |
| 3 | 50 | 75 | 5 | 150 |
| 4 | 50 | 85 | 5 | 128 |
| 5 | 87 | 103 | 1 | 192 |
| 6 | 91 | 130 | 1 | 205 |
| 7 | 150 | 220 | 1 | 42 |

The reaction mass is then redistilled on a 1' Goodloe silver mirror column to yield the following fractions:

| Fraction Number | Vapor Temp. (°C.) | Liquid Temp. (°C.) | Head Vac. mm Hg. | Reflux Ratio | Weight of Fraction |
|---|---|---|---|---|---|
| 1 | 25/20 | 50/52 | 1/6 | 4:1 | 41 |
| 2 | 24 | 78 | 5 | 4:1 | 47 |
| 3 | 53 | 83 | 4 | 4:1 | 20 |
| 4 | 50 | 88 | 2 | 4:1 | 76 |
| 5 | 59 | 90 | 2 | 4:1 | |
| 6 | 73 | 160 | 2 | 1:3 | 87 |
| 7 | 63 | 163 | 2 | 1:3 | 40 |
| 8 | | 220 | 2 | 1:3 | 4 |

GLC, NMR and IR analysis yield the information that the reaction product contains compounds having the structures:

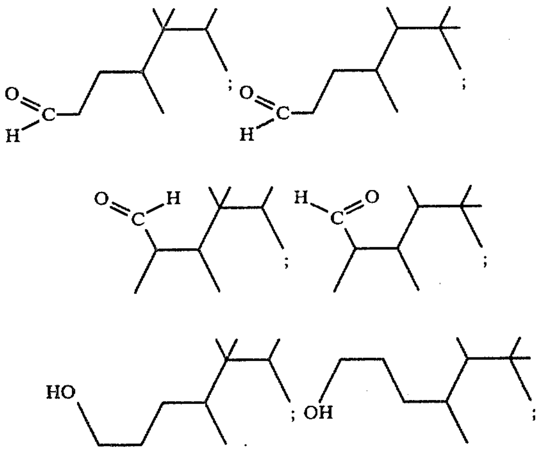

-continued

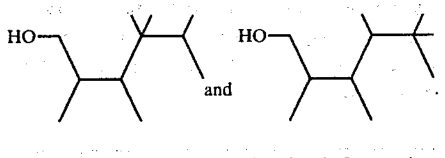

and

GLC, NMR and IR analyses yield the information that fractions 3 and 4 and 5 represent diisoundecanal isomers having structures:

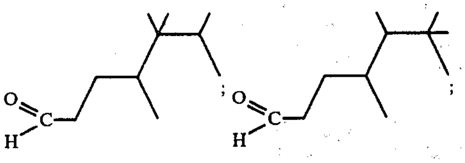

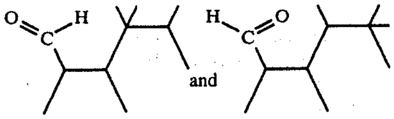

and whereas fractions 6, 7 and 8 of the foregoing distillation contain diisoundecanol isomers having the structures:

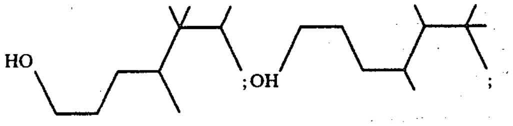

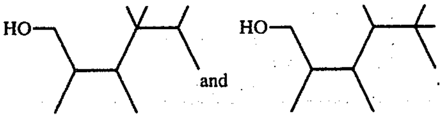

and

Figure 5:
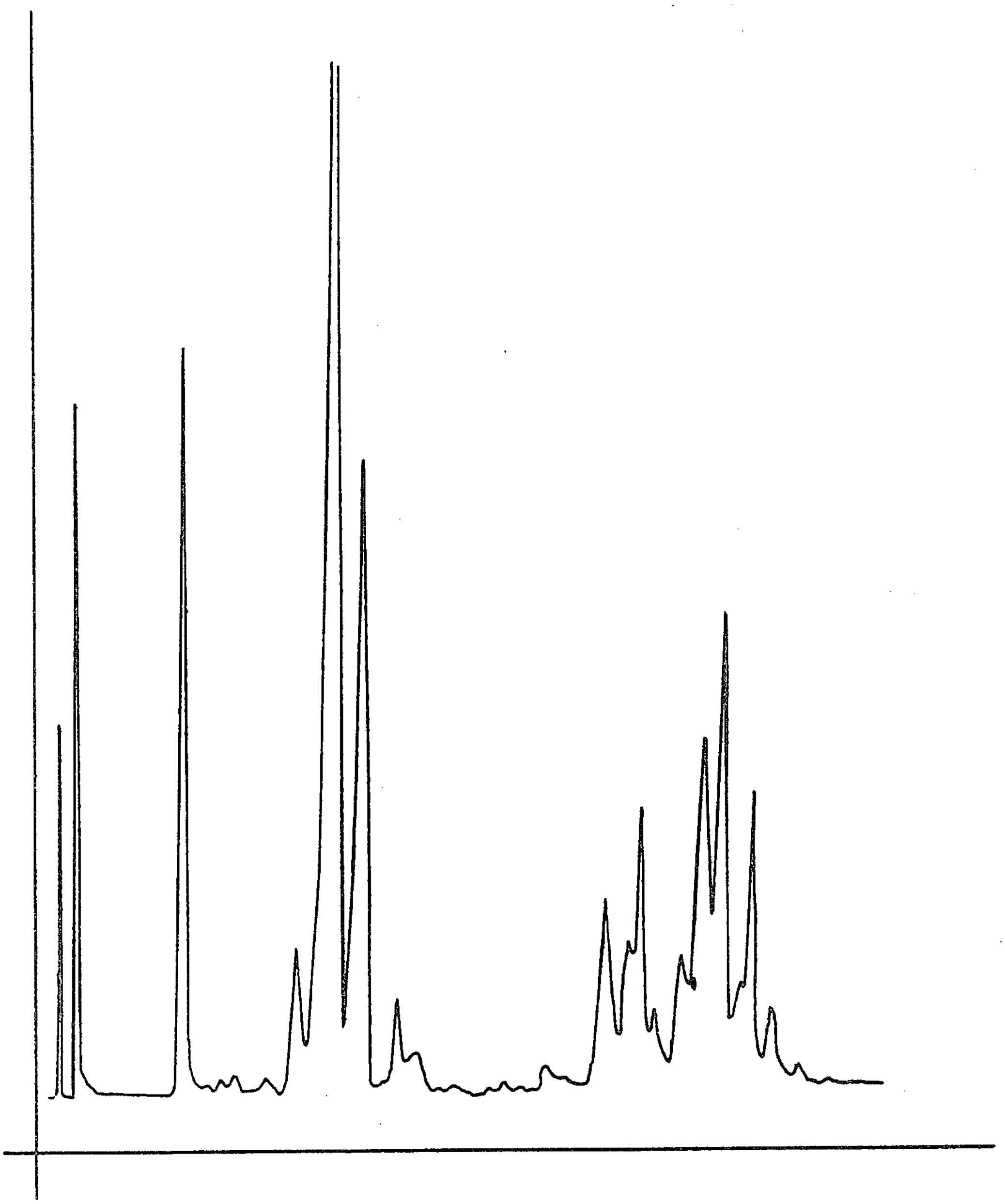
FIG. 5 is the GLC profile for the crude reaction product produced according to Example II (conditions: SF 96 column, 6'×¼", programmed at 180° C., isothermal) containing the compounds having the structures.

FIG. 5 is the GLC profile for the crude reaction product produced according to Example II (conditions: SF 96 column, 6'×¼", programmed at 180° C., isothermal) containing the compounds having the structures:

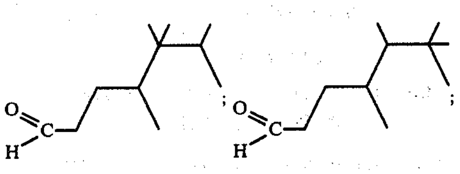

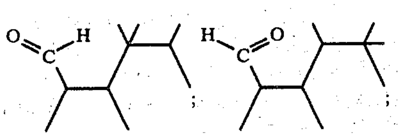

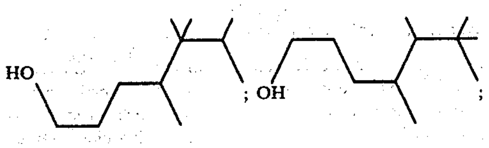

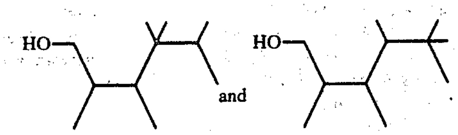

and

FIG. 6 is the GLC profile for the diisoundecanal compounds produced according to Example II having the structures:

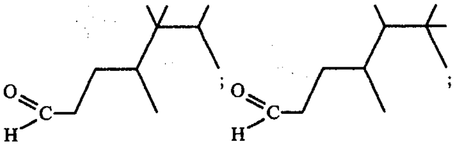

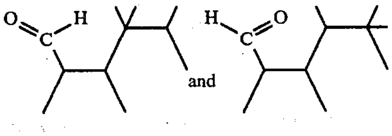

and

FIG. 7 is the NMR spectrum for the diisoundecanal compounds produced according to Example II having the structures:

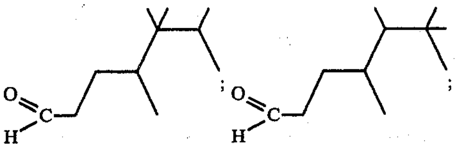

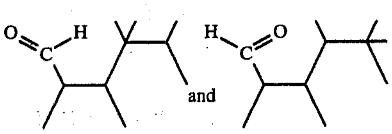

and

FIG. 8 is the infra-red spectrum for the diisoundecanal compounds produced according to Example II having the structures:

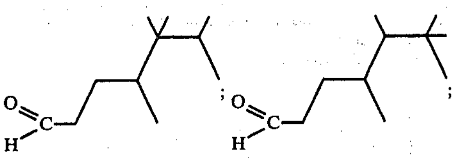

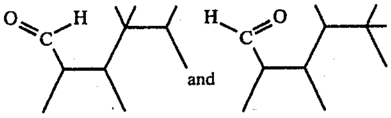

and

FIG. 9 is the GLC profile (conditions: SF-96, 6"×¼" 180° C. isothermal column) produced according to Example II containing the compounds having the structures:

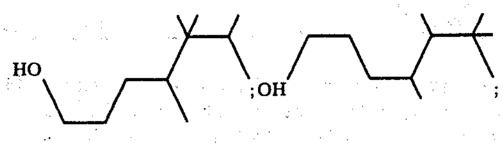

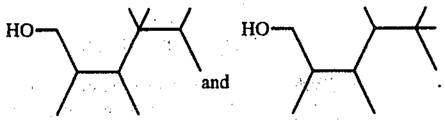

and

FIG. 10 is the NMR spectrum for the diisoundecanol compounds produced according to Example II having the structures:

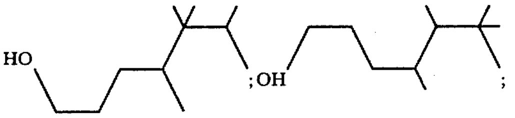

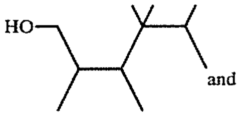

and

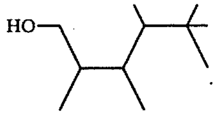

FIG. 11 is the infra-red spectrum for the diisoundecanol compounds produced according to Example II having the structures:

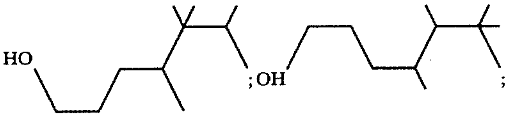

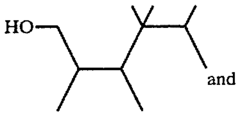

and

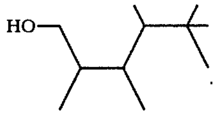

EXAMPLE III

CITRUS COLOGNE

The following citrus cologne formulation is prepared:

| Ingredients | Parts by Weight |
|---|---|
| Mixture of diisoundecanal compounds having the structures: 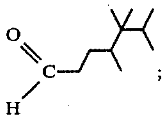 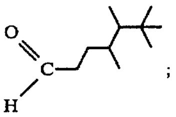 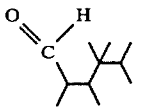 and 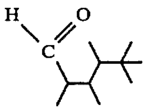 (fractions 3, 4 and 5 of the distillation product of the reaction product of Example II) | 600 |
| Bergamot oil | 100 |
| Phenyl ethyl alcohol | 100 |
| Hydroxy citronelal | 100 |
| Benzyl salicylate | 100 |

The diisoundecanals produced according to Example II impart to this citrus cologne formulation an intense, long-lasting citrusy, green, melony aroma with excellent dry, woody nuances.

EXAMPLE IV

The diisoundecanols produced according to Example II (fractions 6, 7 and 8) have peanut oil-like aromas becoming strongly vetiver on dry-out. These peanut oil and vetiver aroma nuances may be utilized to a great extent in inexpensive functional products. The following pine fragrance demonstrates the use of this material in perfume compositions. In this case it is used at a rate of 47.9%:

| Ingredients | Parts by Weight |
|---|---|
| Diisoundecanols produced according to Example II having the structures: 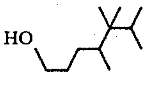 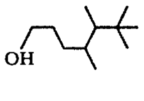 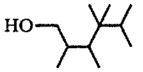 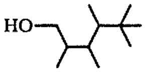 (fractions 6, 7 and 8 produced according to Example II) | 479 |
| Isoburnyl acetate | 100 |
| Camphor | 10 |
| Terpineol | 25 |
| Fir balsam absolute (50% in diethyl phthalate) | 20 |
| Coumarin | 4 |
| Linalool | 30 |
| Anethol | 2 |
| Fenchyl alcohol | 10 |
| Lemon terpenes washed | 50 |
| Borneol | 5 |
| Galbanum oil | 5 |
| Turpentine Russian | 150 |
| *Pinus pumilionus* | 50 |
| Eucalyptol | 50 |
| 2,2,6-trimethyl-1-cyclohexene-1-carboxaldehyde | 5 |
| Maltol 1% in diethyl phthalate | 5 |

The presence of the diisoundecanols prepared according to Example II supports the pine notes and imparts a strong, vetiver character, particularly on dry-out, thus producing a considerable savings in the cost of the formulation. In addition, this piney formulation is enhanced with the vetiver and peanut oil aroma nuances.

EXAMPLE V

PREPARATION OF COSMETIC POWDER COMPOSITIONS

Cosmetic powder compositions are prepared by mixing in a ball mill, 100 grams of talcum powder (per composition) with 0.25 grams of the substance set forth in Table I below (per composition). Each of the cosmetic powder compositions has an excellent aroma as described in Table I below:

TABLE I

| Substance | Aroma Description |
|---|---|
| Mixture prepared according to Example I prior to second distillation but subsequent to splash column distillation. | A citrusy, green, melony, dry woody, vetiver aroma becoming more vetiver on dry-out. |
| Mixture of diisoundecanals prepared according to Example II, distillation fractions 3, 4 and 5 having the structures: | A citrusy, green, melony aroma with dry woody nuances. |

TABLE I-continued

| Substance | Aroma Description |
|---|---|
| 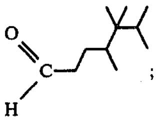 ; 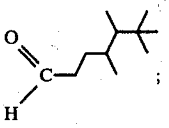 ; 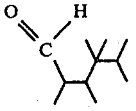 and 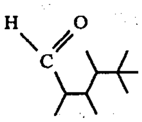 | |
| Mixture of diisoundecanols produced according to Example II, fractions 6, 7 and 8 having the structures: 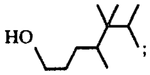 ; 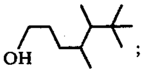 ; 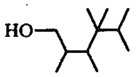 and 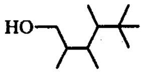 | A peanut oil-like aroma becoming strongly vetiver-like on dry-out. |
| Perfume composition of Example III. | A strong, citrusy aroma with green, melony and dry woody nuances. |
| Perfume composition prepared according to Example IV. | A piney aroma having vetiver nuances and becoming piney/vetiver-like on dry-out. |

EXAMPLE VI

PERFUMED LIQUID DETERGENTS

Concentrated liquid detergents (Lysine salt of n-dodecylbenzene sulfonic acid as more specifically described in U.S. Pat. No. 3,948,818, issued on Apr. 6, 1976) with aroma nuances as set forth in Table II below, are prepared containing 0.10%, 0.15%, 0.20%, 0.25%, 0.30% and 0.35% of the substance set forth in Table II below. They are prepared by adding and homogeneously mixing the appropriate quantity of substance set forth in Table II below in the liquid detergent. The detergents all possess excellent aromas as set forth in Table II below, the intensity increasing with greater concentrations of substance as set forth in Table II below:

TABLE II

| Substance | Aroma Description |
|---|---|
| Mixture prepared according to Example I prior to second distillation but subsequent to splash column distillation. | A citrusy, green, melony, dry woody, vetiver aroma becoming more vetiver on dry-out. |
| Mixture of diisoundecanals prepared according to Example II, distillation fractions 3, 4 and 5 having the structures: 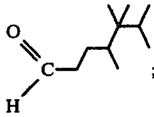 ; 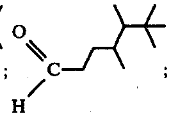 ; 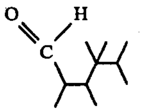 and 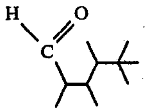 | A citrusy, green, melony aroma with dry woody nuances. |
| Mixture of diisoundecanols produced according to Example II, fractions 6, 7 and 8 having the structures: 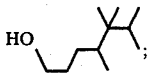 ; 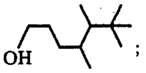 ; 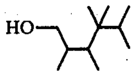 and 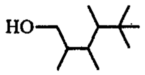 | A peanut oil-like aroma becoming strongly vetiver-like on dry-out. |
| Perfume composition of Example III. | A strong, citrusy aroma with green, melony and dry woody nuances. |
| Perfume composition prepared according to Example IV. | A piney aroma having vetiver nuances and becoming piney/vetiver-like on dry-out. |

EXAMPLE VII

PREPARATION OF COLOGNES AND HANDKERCHIEF PERFUMES

Compositions as set forth in Table III below are incorporated into colognes at concentrations of 2.0%, 2.5%, 3.0%, 3.5%, 4.0%, 4.5% and 5.0% in 85%, 90% and 95% aqueous food grade ethanol solutions; and into handkerchief perfumes at concentrations of 15%, 20%, 25% and 30% (in 85%, 90% and 95% aqueous food grade ethanol solutions). Distinctive and definitive fragrances as set forth in Table III below are imparted to the colognes and to the handkerchief perfumes at all levels indicated above;

TABLE III

| Substance | Aroma Description |
|---|---|
| Mixture prepared according to Example I prior to second distillation but subsequent to splash column distillation. | A citrusy, green, melony, dry woody, vetiver aroma becoming more vetiver on dry-out. |
| Mixture of diisoundecanals prepared according to Example II, distillation fractions 3, 4 and 5 having the structures: 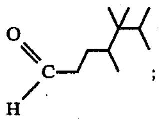 ; 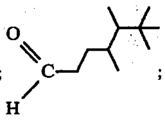 ; 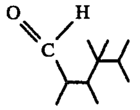 and 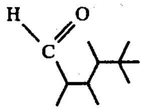 | A citrusy, green, melony aroma with dry woody nuances. |
| Mixture of diisoundecanols produced according to Example II, fractions 6, 7 and 8 having the structures: | A peanut oil-like aroma becoming strongly vetiver-like on dry-out. |

TABLE III-continued

| Substance | Aroma Description |
|---|---|
| 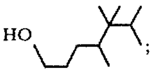 ; 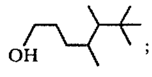 ; 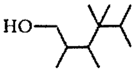 and 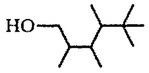 | |
| Perfume composition of Example III. | A strong, citrusy aroma with green, melony and dry woody nuances. |
| Perfume composition prepared according to Example IV. | A piney aroma having vetiver nuances and becoming piney/vetiver-like on dry-out. |

EXAMPLE VIII

PREPARATION OF SOAP COMPOSITIONS

One hundred grams of soap chips per sample (Ivory ®, produced by the Procter & Gamble Company of Cincinnati, Ohio) are each mixed with one gram samples of substances as set forth in Table IV below until homogeneous compositions are obtained. In each of the cases the homogeneous compositions are heated under three atmospheres pressure at 180° C. for a period of three hours and the resulting liquids are placed into soap molds. The resulting soap cakes, on cooling, manifest aromas as set forth in Table IV below:

TABLE IV

| Substance | Aroma Description |
|---|---|
| Mixture prepared according to Example I prior to second distillation but subsequent to splash column distillation | A citrusy, green, melony, dry woody, vetiver aroma becoming more vetiver on dry-out. |
| Mixture of diisoundecanals prepared according to Example II, distillation fractions 3, 4 and 5 having the structures: 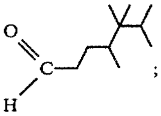 ; 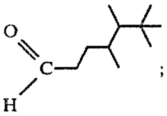 ; 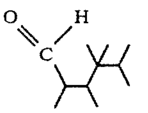 and 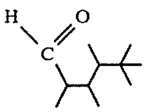 | A citrusy, green, melony aroma with dry woody nuances. |
| Mixture of diisoundecanols produced according to Example II, fractions 6, 7 and 8 having the structures: 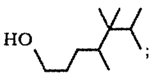 ; 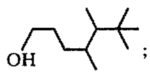 ; 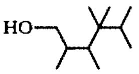 and 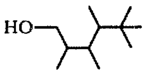 | A peanut oil-like aroma becoming strongly vetiver-like on dry-out. |
| Perfume composition of Example III. | A strong, citrusy aroma with green, melony and dry woody nuances. |

TABLE IV-continued

| Substance | Aroma Description |
|---|---|
| Perfume composition prepared according to Example IV. | A piney aroma having vetiver nuances and becoming piney/vetiver-like on dry-out. |

EXAMPLE IX

PREPARATION OF SOLID DETERGENT COMPOSITIONS

Detergents are prepared using the following ingredients according to Example I of Canadian Pat. No. 1,007,948:

| Ingredient | Percent by Weight |
|---|---|
| "Neodol ® 45-11 (a $C_{14}$-$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table V below. Each of the detergent samples has excellent aromas as indicated in Table V below:

TABLE V

| Substance | Aroma Description |
|---|---|
| Mixture prepared according to Example I prior to second distillation but subsequent to splash column distillation. | A citrusy, green, melony, dry woody, vetiver aroma becoming more vetiver on dry-out. |
| Mixture of diisoundecanals prepared according to Example II, distillation fractions 3, 4 and 5 having the structures: 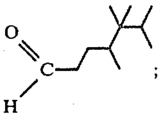 ; 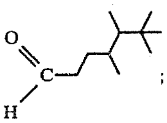 ; 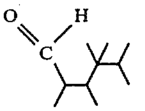 and 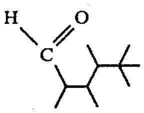 | A citrusy, green, melony aroma with dry woody nuances. |
| Mixture of diisoundecanols produced according to Example II, fractions 6, 7 and 8 having the structures: 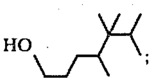 ; 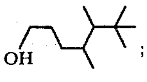 ; 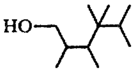 and 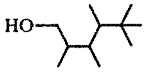 | A peanut oil-like aroma becoming strongly vetiver-like on dry-out. |
| Perfume composition of Example III. | A strong, citrusy aroma with green, melony and dry woody nuances. |
| Perfume composition prepared | A piney aroma having |

TABLE V-continued

| Substance | Aroma Description |
|---|---|
| according to Example IV. | vetiver nuances and becoming piney/vetiver-like on dry-out. |

EXAMPLE X

Utilizing the procedure of Example I at column 15 of U.S. Pat. No. 3,632,396, nonwoven cloth substrates useful as dry-added fabric softening articles of manufacture are prepared wherein the substrate, the substrate coating and the outer coating and the perfuming material are as follows:

1. A water "dissolvable" paper ("Dissolvo Paper")
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table VI below Fabric softening compositions prepared according to Example I at column 15 of U.S. Pat. No. 3,632,396 having aroma characteristics as set forth in Table VI below, consist of a substrate coating having a weight of about 3 grams per 100 square inches of substrate; a first coating consisting of about 1.85 grams per 100 square inches of substrate; and an outer coating consisting of about 1.4 grams per 100 square inches of substrate. The substance of Table VI below is admixed with the outer coating mixture thereby providing a total aromatized outer coating weight ratio to substrate of about 1:1 by weight of the substrate. The aroma characteristics are imparted in a pleasant manner to the head space in the dryer on operation thereof using the said dryer-added fabric softening non-woven fabrics:

TABLE VI

| Substance | Aroma Description |
|---|---|
| Mixture prepared according to Example I prior to second distillation but subsequent to splash column distillation. | A citrusy, green, melony, dry woody, vetiver aroma becoming more vetiver on dry-out. |
| Mixture of diisoundecanals prepared according to Example II, distillation fractions 3, 4 and 5 having the structures: 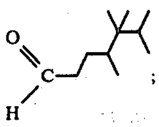 ; 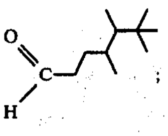 ; 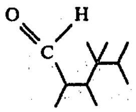 and 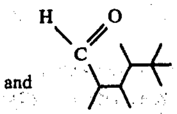 | A citrusy, green, melony aroma with dry woody nuances. |
| Mixture of diisoundecanols produced according to Example II, fractions 6, 7 and 8 having the structures: | A peanut oil-like aroma becoming strongly vetiver-like on dry-out. |

TABLE VI-continued

| Substance | Aroma Description |
|---|---|
| 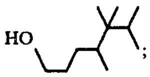 ; 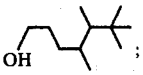 ; 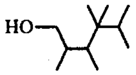 and 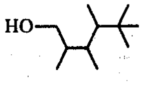 | |
| Perfume composition of Example III. | A strong, citrusy aroma with green, melony and dry woody nuances. |
| Perfume composition prepared according to Example IV. | A piney aroma having vetiver nuances and becoming piney/vetiver-like on dry-out. |

EXAMPLE XI

HAIR SPRAY FORMULATION

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI Americas Corporation) | 0.03 weight percent |
| Perfuming substance as set forth in Table VII | 0.10 weight percent |

The perfuming substance as set forth in Table VII adds an aroma characteristic as set forth in Table VII which is rather intense and esthetically pleasing to the user of the soft-feel, good-hold pump hair spray:

TABLE VII

| Substance | Aroma Description |
|---|---|
| Mixture prepared according to Example I prior to second distillation but subsequent to splash column distillation. | A citrusy, green, melony, dry woody, vetiver aroma becoming more vetiver on dry-out. |
| Mixture of diisoundecanals prepared according to Example II, distillation fractions 3, 4 and 5 having the structures: 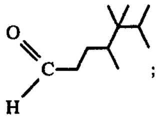 ; 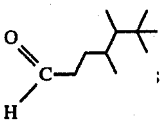 ; 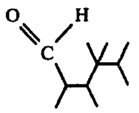 and 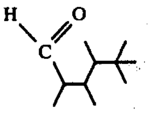 | A citrusy, green, melony aroma with dry woody nuances. |
| Mixture of diisoundecanols produced according to Example II, fractions 6, 7 and 8 having the | A peanut oil-like aroma becoming strongly vetiver-like on dry-out. |

TABLE VII-continued

| Substance | Aroma Description |
| --- | --- |
| structures: 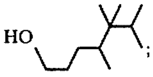 ; 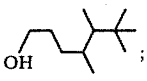 ; 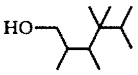 and 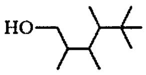 | |
| Perfume composition of Example III. | A strong, citrusy aroma with green, melony and dry woody nuances. |
| Perfume composition prepared according to Example IV. | A piney aroma having vetiver nuances and becoming piney/vetiver-like on dry-out. |

EXAMPLE XII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

Gafquat® 755 N polymer (manufactured by GAF Corporation of 140 West 51st Street, New York, N,Y.) (5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table VIII below is added to the mixture. The resulting mixture is cooled to 40° C. and blending is carried out for an additional one hour. At the end of this blending period, the resulting material has a pleasant fragrance as indicated in Table VIII below:

TABLE VIII

| Substance | Aroma Description |
| --- | --- |
| Mixture prepared according to Example I prior to second distillation but subsequent to splash column distillation. | A citrusy, green, melony, dry woody, vetiver aroma becoming more vetiver on dry-out. |
| Mixture of diisoundecanals prepared according to Example II, distillation fractions 3, 4 and 5 having the structures: 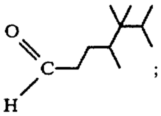 ; 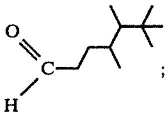 ; 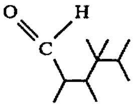 and 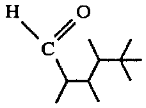 | A citrusy, green, melony aroma with dry woody nuances. |
| Mixture of diisoundecanols produced according to Example II, fractions 6, 7 and 8 having the structures: 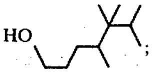 ; 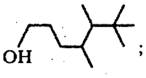 ; 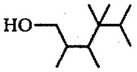 and 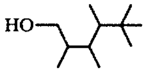 | A peanut oil-like aroma becoming strongly vetiver-like on dry-out. |
| Perfume composition of Example III. | A strong, citrusy aroma with green, melony and dry woody nuances. |
| Perfume composition prepared according to Example IV. | A piney aroma having vetiver nuances and becoming piney/vetiver-like on dry-out. |

What is claimed is:

1. A compound defined according to the structure:

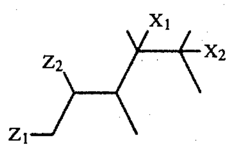

wherein one of $X_1$ or $X_2$ is hydrogen and the other of $X_1$ or $X_2$ is methyl; and wherein one of $Z_1$ or $Z_2$ is hydrogen and the other of $Z_1$ or $Z_2$ is hydroxymethyl having the structure:

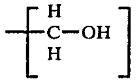

or carboxaldehyde having the structure:

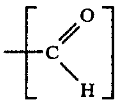

2. A process comprising reacting at least one compound having a structure selected from the group consisting of:

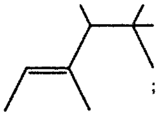 ; 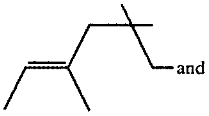 and 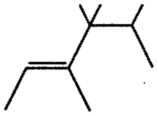

with a mixture of carbon monoxide and hydrogen in the presence of an oxo reaction catalyst at a temperature in the range of from 150° up to 300° C.; and at a pressure in the range of from 50 atmospheres up to 250 atmospheres, the mole ratio of carbon monoxide:hydrogen being from 0.1:1 up to 1:0.1 thereby producing at least one product defined according to claim 1.

3. The product produced according to the process of claim 2.
4. The process of claim 2 whereby the substances defined according to the structures:
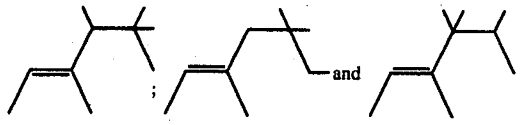
are prepared by dimerizing isoamylene in the presence of an acid, thereby producing at least one product defined according to claim 1.
5. The product produced according to the process of claim 4.
* * * * *